United States Patent [19]
Flynn et al.

[11] Patent Number: 5,731,306
[45] Date of Patent: Mar. 24, 1998

[54] MERCAPTOACETYLAMIDO 1,3,4,5-TETRAHYDRO-BENZO[C]AZEPIN-3-ONE DISULFIDE DERIVATIVES USEFUL AS INHIBITORS OF ENKEPHALINASE AND ACE

[76] Inventors: Gary A. Flynn, 7121 Euclid Rd., Cincinnati, Ohio 45243; Douglas W. Beight, 645 Glensprings Dr., Cincinnati, Ohio 45246; Alan M. Warshawsky, 10713 Shadowcrest Ct., Cincinnati, Ohio 45242; Shujaath Mehdi, 6430 Welton St., Cincinnati, Ohio 45213; John F. French, 3619 Sherbrooke Dr., Cincinnati, Ohio 45241; John H. Kehne, 430 E. Sharon Rd., Cincinnati, Ohio 45246

[21] Appl. No.: 673,250

[22] Filed: Jun. 26, 1996

Related U.S. Application Data

[63] Continuation of Ser. No. 371,669, Jan. 12, 1995, abandoned, which is a continuation of Ser. No. 226,799, Apr. 12, 1994, abandoned, which is a continuation-in-part of Ser. No. 195,407, Feb. 14, 1994, abandoned.

[51] Int. Cl.$^6$ ............................ A61K 31/55; C07D 498/04
[52] U.S. Cl. ..................................... 514/213; 540/523
[58] Field of Search ................................ 514/212, 213; 540/523

[56] References Cited

U.S. PATENT DOCUMENTS

| | | |
|---|---|---|
| 3,334,091 | 8/1967 | Houlihan . |
| 3,334,095 | 8/1967 | Houluhan . |
| 4,320,057 | 3/1982 | Freed et al. . |
| 4,391,752 | 7/1983 | Crossley . |
| 4,399,136 | 8/1983 | Hassall et al. . |
| 4,415,496 | 11/1983 | Harris et al. . |
| 4,487,929 | 12/1984 | Hassall et al. . |
| 4,512,924 | 4/1985 | Attwood et al. . |
| 4,584,294 | 4/1986 | Ruyle . |
| 4,658,024 | 4/1987 | Attwood et al. . |
| 4,692,438 | 9/1987 | Hassall et al. . |
| 4,716,232 | 12/1987 | Ternansky . |
| 4,734,504 | 3/1988 | Holmes . |
| 4,734,505 | 3/1988 | Holmes . |
| 4,762,924 | 8/1988 | Hassall et al. . |
| 4,772,701 | 9/1988 | Attwood et al. . |
| 4,782,149 | 11/1988 | Lawton et al. . |
| 4,785,093 | 11/1988 | Hassall et al. . |
| 4,808,713 | 2/1989 | Attwood et al. . |
| 4,824,832 | 4/1989 | Flynn et al. . |
| 4,826,980 | 5/1989 | Hassall et al. . |
| 4,879,309 | 11/1989 | Doll et al. ........................ 514/513 |
| 4,973,585 | 11/1990 | Flynn et al. . |
| 5,208,230 | 5/1993 | Flynn et al. ..................... 514/214 |
| 5,238,932 | 8/1993 | Flynn et al. ..................... 514/214 |
| 5,252,601 | 10/1993 | Flynn et al. ..................... 514/465 |
| 5,308,841 | 5/1994 | Flynn et al. ..................... 514/215 |
| 5,366,973 | 11/1994 | Flynn et al. ..................... 514/221 |
| 5,389,628 | 2/1995 | Flynn et al. ..................... 514/215 |
| 5,420,271 | 5/1995 | Warshawsky et al. ........... 540/521 |
| 5,424,425 | 6/1995 | Flynn et al. ..................... 540/521 |
| 5,428,158 | 6/1995 | Warshawsky et al. ........... 540/214 |
| 5,430,145 | 7/1995 | Flynn et al. ..................... 540/521 |
| 5,455,242 | 10/1995 | Warshawsky et al. ........... 514/545 |
| 5,457,196 | 10/1995 | Warshawsky et al. ........... 540/521 |

FOREIGN PATENT DOCUMENTS

| | | |
|---|---|---|
| 0128728 | 12/1984 | European Pat. Off. . |
| 0249223 | 12/1987 | European Pat. Off. . |
| 0249224 | 12/1987 | European Pat. Off. . |
| 0322914 | 12/1988 | European Pat. Off. . |
| 0534396 | 3/1992 | European Pat. Off. . |
| 0481522 | 4/1992 | European Pat. Off. . |
| 0492369 | 7/1992 | European Pat. Off. . |
| 0533084 | 9/1992 | European Pat. Off. . |
| 0599444 | 6/1994 | European Pat. Off. . |
| 0657453 | 6/1995 | European Pat. Off. . |
| 9108195 | 6/1991 | WIPO . |
| 9109840 | 7/1991 | WIPO . |
| 9302099 | 2/1993 | WIPO . |
| 9410193 | 9/1993 | WIPO . |

OTHER PUBLICATIONS

Flynn, et al., J. Am. Chem. Soc. 109, 7914 (1987).
Flynn, et al., Tetrahedron Letters, vol. 31 (6), 815–88 (1990).
Attwood, et al., J. Chem. Soc. Perkin Trans. I, pp. 1011–1019 (1986).
Natoff, et al., Drugs of the Future, vol. 12 (5): 475–483 (1987).
J. Med. Chem., 1992, 35, 823–832, Timothy D. Ocain et al.
Bioorganic and Medical Chem. Letters, vol. 1, 309, 1991.
W.H. Parsons et al. Biochemical and Biophysical Research Communications vol. 117, No. 1, 1993.
Fournie–Zaluski, Marie–Claude et al., J. Med. Chem., 1992, vol. 35, pp. 2473–2481, 1259–1266.
French, John F., Jour. of Pharm and Exper. Therapeutics, vol. 268, No. 1, pp. 180–186, (1986).
Powell Jerry S. et al., Journal of American College of Cardiology, vol. 17, No. 6, pp. 137B–142B (May 1991).

(List continued on next page.)

Primary Examiner—Shean C. Wu

[57] ABSTRACT

The present invention relates to certain novel mercaptoacetylamido 1,3,4,5-tetrahydro-benzo[c]azepin-3-one disulfide derivatives of the formula

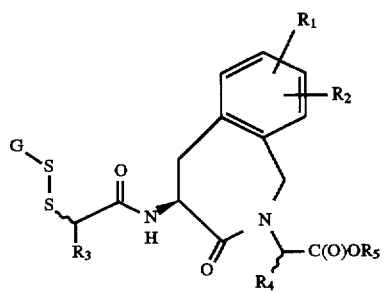

useful as inhibitors of enkephalinase and of ACE.

18 Claims, No Drawings

OTHER PUBLICATIONS

Davis, Harry R. et. al., *Supplement I Circulation*, vol. 86, No. 4 p. I-220(0873), (Oct. 1992).

Burkholder, et al., *Bioorganic and Medical Chem. Letters*, vol. 3, No. 2, pp. 231–234, 1993.

Flynn et al., *J. Med. Chem.*, 1993, 36 2420–2423.

34th Nat'l Organic Symposium, Williamsburg, VA, Jun. 11–15, 1995 (poster #133).

ACS Meeting—Aneheim, CA Apr. 2–7, 1995 (poster #161).

ACS Meeting in Chicago, IL Aug. 24, 1995 (poster No. 64).

MERCAPTOACETYLAMIDO 1,3,4,5-TETRAHYDRO-BENZO[C]AZEPIN-3-ONE DISULFIDE DERIVATIVES USEFUL AS INHIBITORS OF ENKEPHALINASE AND ACE

This is a continuation of application Ser. No. 08/371,669, filed Jan. 12, 1995, now abandoned, which is a continuation of application Ser. No. 08/226,799 filed Apr. 12, 1994, now abandoned; which is a continuation-in-part of application Ser. No. 08/195,407, filed Feb. 14, 1994, now abandoned.

BACKGROUND OF THE INVENTION

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would also be useful in the treatment of irritable bowel syndrome.

ANP refers to a family of naturally-occurring peptides which are involved in the homeostatic regulation of blood pressure, as well as sodium and water levels. ANP have been found to vary in length from about 21 to about 126 amino acids with a common structural feature being one or more disulfide-looped sequences of 17 amino acids with various amino- and carboxy-terminal sequences attached to the cysteine moiety. ANP have been found to bind to specific binding sites in various tissues including kidney, adrenal, aorta, and vascular smooth muscle with affinities ranging from about 50 pico-molar (pM) to about 500 nano-molar (nM) [Needleman, *Hypertension* 7, 469 (1985)]. In addition, it is believed that ANP binds to specific receptors in the brain and possibly serves as a neuromodulator as well as a conventional peripheral hormone.

The biological properties of ANP involve potent diuretic/natriuretic and vasodilatory/hypotensive effects as well as an inhibitory effect on renin and aldosterone secretion [deBold, *Science* 230, 767 (1985)]. By inhibiting enkephalinase, the metabolic degradation of the naturally-occurring ANP are inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

In addition, the compounds of the present invention are inhibitors of Angiotensin-Converting Enzyme (ACE). ACE is a peptidyl dipeptidase which catalyzes the conversion of angiotensin I to angiotensin II. Angiotensin II is a vasoconstrictor which also stimulates aldosterone secretion by the adrenal cortex. Inhibition of ACE would therefore be useful in a patient suffering from disease states such as hypertension and congestive heart failure [See William W. Douglas, "Polypeptides-Angiotensin, Plasma Kinins, and Others", Chapter 27, in *Goodman and Gillman's the Pharmacological Basis of Therapeutics*, 7th edition, 1985, pp. 652–3, MacMillan Publishing Co., New York, N.Y.]. In addition, it has been discovered that ACE inhibitors are useful in treating cognitive disorders [German Application No. 3901-291-A, published Aug. 3, 1989].

In addition, the compounds of the present invention are useful as inhibitors of smooth cell proliferation. Smooth muscle cell proliferation in the intima of muscular arteries is a primary cause of vascular stenosis in arteriosclerosis, after vascular surgery, and after coronary angioplasy. Several animal studies have indicated the renin-angiotensin system plays an important role in this vascular response to injury. Chronic treatment with angiotensin converting enzyme (ACE) inhibitors reduced myointimal thickening following balloon injury in rat carotid artery or aorta. Powell, J. S., Muller, R. K. M. and Baumgartner, H. R.; Suppression of the vascular response to injury: The role of angiotensin-converting enzyme inhibitors. *J. Am. Coll. Cardiol.* 17:137B-42B, 1991. More recently, atrial natruiuretic peptide (ANP) has been found to decrease myointimal proliferation. ANP is rapidly metabolized by receptor mediated clearance and by neutral endopeptidase (NEP). Inhibition of NEP significantly reduces proliferation in the balloon-injured rabbit vasculature. Davis, H. R., McGregor, D. C., Hoos, L., Mullins, D. E. and Sybertz, E. J.: Atrial naturiuretic factor and the neutral endopeptidase inhibitor SCH42495 prevent myointimal proliferation after vascular injury. Circ. 86:I-220, 1992. These studies imply that a dual inhibitor of ACE and NEP should be therapeutically useful in the treatment of conditions which require inhibition of smooth cell proliferation. Davis and Sybertz, European Patent Application 533084-A1, Mar. 24, 1993.

SUMMARY OF THE INVENTION

The present invention provides novel compounds of the Formula (I)

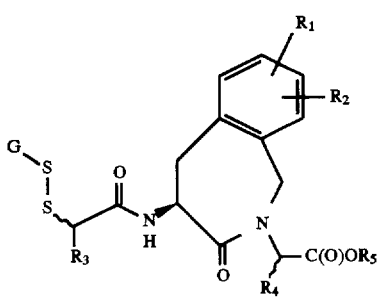

Formula (I)

wherein

R$_1$ and R$_2$ are each independently hydrogen, hydroxy, —OR$_6$ wherein R$_6$ is a C$_1$-C$_4$ alkyl or an Ar—Y— group wherein Ar is aryl and Y is a C$_0$-C$_4$ alkyl; or, where R$_1$ and R$_2$ are attached to adjacent carbon atoms, R$_1$ and R$_2$ can be taken together with said adjacent carbons to form a benzene ring, or methylenedioxy;

R$_3$ is hydrogen, C$_1$-C$_8$ alkyl, —CH$_2$OCH$_2$CH$_2$OCH$_3$, or an Ar—Y— group;

R$_4$ is hydrogen, C$_1$-C$_6$ alkyl, an Ar—Y— group, —CH$_2$CH$_2$SCH$_3$, CH$_2$OH, CH(OH)CH$_3$, CH$_2$CH$_2$C(=O)NH$_2$, CH$_2$C(=O)NH$_2$, or a group of the formula

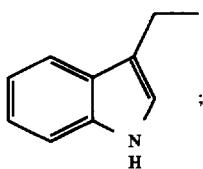

R$_5$ is hydrogen, a C$_1$-C$_4$ alkyl or an Ar—Y— group, or —CH$_2$O—C(O)C(CH$_3$)$_3$;

G is a radical chosen from the group;

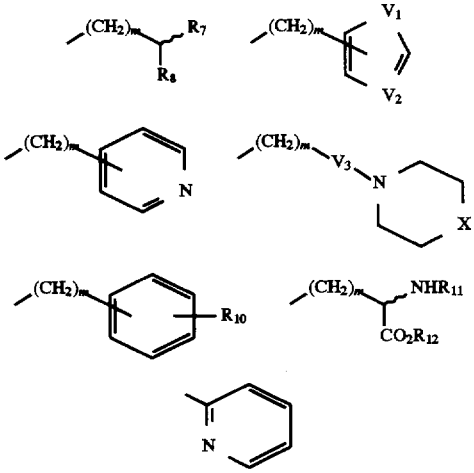

wherein m is an integer from 1 to 3;

R$_7$ is hydrogen, C$_1$-C$_6$ alkyl, —CH$_2$CH$_2$S(O)$_p$CH$_3$, or arylalkyl wherein p is 0, 1 or 2;

R$_8$ is hydrogen, hydroxy, amino, C$_1$-C$_6$ alkyl, N-methylamino, N,N-dimethylamino, —CO$_2$R$_5$, or —OC(O)R$_9$ wherein R$_9$ is hydrogen, C$_1$-C$_6$ alkyl, or phenyl;

R$_{10}$ is 1 or 2 substituents independently chosen from the group consisting of; hydrogen, C$_1$-C$_4$ alkyl, C$_1$-C$_4$ alkoxy, or halogen;

R$_{11}$ is hydrogen, C$_1$-C$_6$ alkyl, or Ar—Y— group;

R$_{12}$ is hydrogen or C$_1$-C$_4$ alkyl;

V$_1$ is O, S, or NH;

V$_2$ is N or CH;

V$_3$ is a direct bond or —C(O)—;

or stereoisomers or pharmaceutically acceptable salts thereof.

The present invention further provides a method of inhibiting enkephalinase in a patient in need thereof comprising administering to said patient an effective enkephalinase inhibitory amount of a compound of Formula (I). The present invention also provides a method of inhibiting ACE in a patient in need thereof comprising administering to said patient an effective ACE inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used in this application:

a) the term "C$_1$-C$_6$ alkyl" refers to a saturated straight or branched chain hydrocarbyl radical of from one to six carbon atoms and includes methyl, ethyl, propyl, isopropyl, n-butyl, isobutyl, tertiary butyl, n-pentyl, cyclo-pentyl, n-hexyl, cyclo-hexyl and the like;

b) the term "C$_1$-C$_4$ alkyl" refers to a saturated straight or branched chain hydrocarbyl radical of from one to six carbon atoms and includes methyl, ethyl, propyl, isopropyl, n-butyl, isobutyl, tertiary butyl;

c) the designation "—◂" refers to a bond that protrudes forward out of the plane of the page;

d) the designation "--◂" refers to a bond that protrudes backward out of the plane of the page;

e) the designation "~~~" refers to a bond for which the stereochemistry is not designated;

f) the term "halogen" refers to a fluorine atom, chlorine atom, bromine atom, or iodine atom;

g) the terms "C$_1$-C$_8$ alkyl" refer to saturated straight or branched chain hydrocarbyl radicals of one to eight and one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like;

h) the term "C$_1$-C$_4$ alkoxy" refer to a straight or branched alkoxy group containing from 1 to 4 carbon atoms, such as methoxy, ethoxy, n-propoxy, isopropoxy, n-butoxy, isobutoxy, t-butoxy, etc;

i) the designation "—C(O)—" refers to a carbonyl group of the formula:

j) the term "Ar—Y—" refers to a radical wherein Ar is an aryl group and Y is a C$_0$-C$_4$ alkyl;

k) the term "C₀-C₄ alkyl" refers to a saturated straight or branched chain hydrocarbyl radical of zero to four carbon atoms and includes a bond, methyl, ethyl, propyl, isopropyl, n-butyl, isobutyl, tertiary butyl and the like;

l) the term "Ar" or "aryl group" refers to a phenyl or naphthyl group unsubstituted or substituted with from one to three substituents selected from the group consisting of methylenedioxy, hydroxy, C₁-C₄ alkoxy, fluoro and chloro; specifically included within the scope of the term "arylalkyl" are phenyl, naphthyl, naphthylmethyl, phenylmethyl or benzyl, phenylethyl, p-methoxybenzyl, 3,4-methylenedioxybenzyl, p-fluorobenzyl and p-chlorobenzyl;

m) the term "alkoxy group" and the alkoxy moiety of an alkoxycarbonyl group can be straight or branched chain and contain from 1 to 8 carbon atoms, preferably from 1 to 4, carbon atoms; specifically included within the scope of the term "alkoxy group" are methoxy, ethoxy, t-butoxy and the like; specific examples of alkoxycarbonyl groups are methoxycarbonyl, ethoxycarbonyl, t-butoxycarbonyl and the like;

n) the term "pharmaceutically acceptable salts" refers to either acid addition salts or to base addition salts.

The expression "pharmaceutically acceptable acid addition salts" is intended to apply to any non-toxic organic or inorganic acid addition salt of a compound of Formula (I) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, and sulfonic acids such as p-toluenesulfonic acid, methane sulfonic acid and 2-hydroxyethane sulfonic acid. Such salts can exist in either a hydrated or substantially anhydrous form.

The expression "pharmaceutically acceptable basic addition salts" is intended to apply to any non-toxic organic or inorganic basic addition salts of a compound of Formula (I) or any of its intermediates. Illustrative bases which form suitable salts include alkali metal or alkaline-earth metal hydroxides such as sodium, potassium, calcium, magnesium, or barium hydroxides; ammonia, and aliphatic, cyclic, or aromatic organic amines such as methylamine, dimethylamine, trimethylamine, triethylamine, diethylamine, isopropyldiethylamine, pyridine and picoline.

As is appreciated by one of ordinary skill in the art the compounds of the Formula (I) may exist as stereoisomers. Any reference in this application to one of the compounds of the Formula (I) is meant to encompass either specific stereoisomers or a mixture of stereoisomers. The specific stereoisomers can be prepared by stereospecific synthesis or can be separated and recovered by techniques known in the art, such as chromatography, chromatography on chiral stationary phases, fractional recrystallization of addition salts formed by reagents used for that purpose, as described in *Enantiomers, Racemates, and Resolutions*, J. Jacques, A. Collet, and S. H. Wilen, Wiley (1981).

Examples of compounds encompassed by the present invention include:

2-[4-(2-Thio-3-phenyl-propionyl-amino)-3-oxo-1,3,4,5-tetrahydro-benzo[c]azepin-2-yl]-4-methyl-valeric acid, (S)-N-1-(2-methylpropyl)-2-(thio)-ethylamine, disulfide;

2-[4-(2-Thio-3-phenyl-propionyl-amino)-3-oxo-1,3,4,5-tetrahydro-benzo[c]azepin-2-yl]-4-methyl-valeric acid, (R)-1-(2-methylpropyl)-2-(thio)-ethylamine, disulfide;

2-[4-(2-Thio-3-phenyl-propionyl-amino)-3-oxo-1,3,4,5-tetrahydro-benzo[c]azepin-2-yl]-4-methyl-valeric acid, L-cysteine ethyl ester, disulfide;

2-[4-(2-Thio-3-phenyl-propionyl-amino)-3-oxo-1,3,4,5-tetrahydro-benzo[c]azepin-2-yl]-4-methyl-valeric acid, N-acetyl-L-cysteine ethyl ester, disulfide;

2-[4-(2-Thio-3-phenyl-propionyl-amino)-3-oxo-1,3,4,5-tetrahydro-benzo[c]azepin-2-yl]-4-methyl-valeric acid, L-cysteine, disulfide;

2-[4-(2-Thio-3-phenyl-propionyl-amino)-3-oxo-1,3,4,5-tetrahydro-benzo[c]azepin-2-yl]-4-methyl-valeric acid, benzylthio, disulfide;

2-[4-(2-Thio-3-phenyl-propionyl-amino)-3-oxo-1,3,4,5-tetrahydro-benzo[c]azepin-2-yl]-4-methyl-valeric acid, ethylthio, disulfide;

2-[4-(2-Thio-3-phenyl-propionyl-amino)-3-oxo-1,3,4,5-tetrahydro-benzo[c]azepin-2-yl]-4-methyl-valeric acid, disulfide, 2-hydroxyethylthio, disulfide;

2-[4-(2-Thio-3-phenyl-propionyl-amino)-3-oxo-1,3,4,5-tetrahydro-benzo[c]azepin-2-yl]-4-methyl-valeric acid, t-butyl ester, 2-pyridylmethylthio, disulfide;

2-[4-(2-Thio-3-phenyl-propionyl-amino)-3-oxo-1,3,4,5-tetrahydro-benzo[c]azepin-2-yl]-4-methyl-valeric acid, 2-thioacetic acid morpholine carboxamide, disulfide;

2-[4-(2-Thio-3-phenyl-propionyl-amino)-3-oxo-1,3,4,5-tetrahydro-benzo[c]azepin-2-yl]-4-methyl-valeric acid, t-butyl ester, benzylthio, disulfide;

2-[4-(2-Thio-3-phenyl-propionyl-amino)-3-oxo-1,3,4,5-tetrahydro-benzo[c]azepin-2-yl]-4-methyl-valeric acid, t-butyl ester, ethylthio, disulfide;

2-[4-(2-Thio-3-phenyl-propionyl-amino)-3-oxo-1,3,4,5-tetrahydro-benzo[c]azepin-2-yl]-4-methyl-valeric acid, t-butyl ester, disulfide, 2-hydroxyethylthio, disulfide;

2-[4-(2-Thio-3-phenyl-propionyl-amino)-3-oxo-1,3,4,5-tetrahydro-benzo[c]azepin-2-yl]-4-methyl-valeric acid, t-butyl ester, 2-pyridylmethylthio, disulfide;

2-[4-(2-Thio-3-phenyl-propionyl-amino)-3-oxo-1,3,4,5-tetrahydro-benzo[c]azepin-2-yl]-4-methyl-valeric acid, t-butyl ester, 2-thioacetic acid morpholine carboxamide, disulfide.

A general synthetic procedure is set forth in Scheme 1 for preparing compounds of Formula (I). In Scheme 1, all substituents unless otherwise indicated, are as previously defined. Starting materials, reagents, techniques, and procedures used in Scheme 1 are well known and appreciated by one of ordinary skill in the art.

SCHEME 1

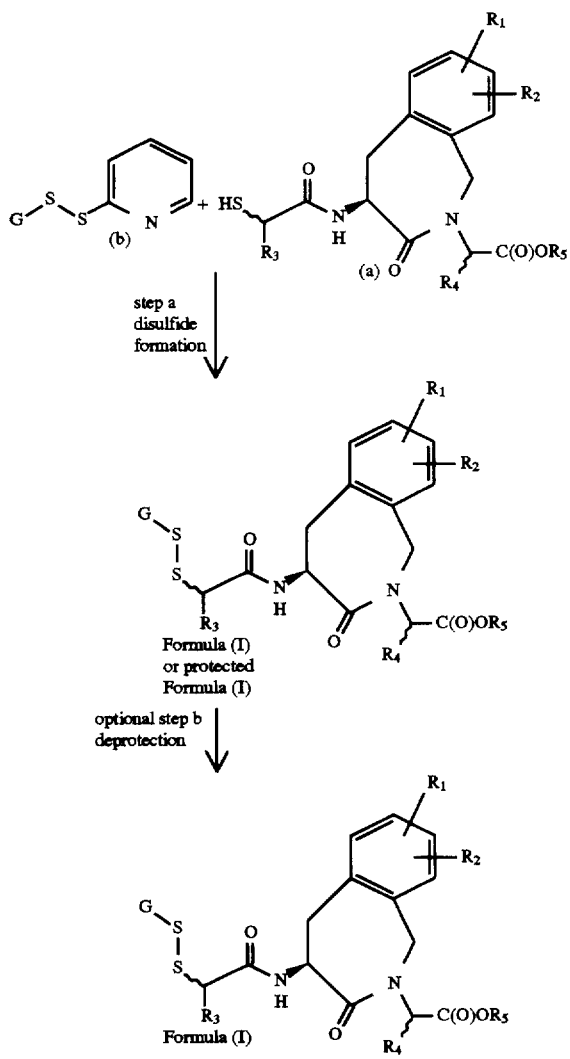

The disulfide of structure (b) can be obtained by methods known in the art or by methods known analogously in the art, B. P. Roques et al *J. Med. Chem.* 33, 2473–2481 (1992). The thiol of structure (a) are prepared according to Scheme A.

In Scheme 1, step a, an appropriate disulfide of structure (b) is contacted with an appropriate thiol of structure (a) to give a disulfide of Formula (I) or a protected disulfide of Formula (I). An appropriate disulfide of structure (b) is one in which G is as desired in the final product of Formula (I) or gives rise upon deprotection to G as is desired in the final product of Formula (I). An appropriate thiol of the structure (a) is one in which $R_1$, $R_2$, $R_3$, $R_4$ and $R_5$ are as desired in the final product of Formula (I) or give rise after deprotection to $R_1$, $R_2$, $R_3$, $R_4$ and $R_5$ as desired in the final product of Formula (I).

For example, an appropriate disulfide of structure (b) is contacted with an appropriate thiol of structure (a). The reaction is carried out in a suitable solvent, such as ethanol, methanol, dichloromethane, or mixtures of ethanol or methanol and dichloromethane. The solvent is degassed by passing a stream of nitrogen gas through it for 15 minutes before the reaction is carried out. The reaction is carried out using from 1.0 to 4.0 molar equivalents of an appropriate compound of structure (b). The reaction is carried out at temperatures of from 0° C. to the refluxing temperature of the solvent, with a temperature of 10° C. to 30° C. being preferred. The reaction generally requires from 1 to 48 hours. The product can be isolated by techniques well known in the art, such as extraction, evaporation, and precipitation. The product can be purified by chromatography and recrystallization.

In Scheme 1, optional step b, a protected disulfide of Formula (I) is deprotected to give a disulfide of Formula (I).

The selection, use, and removal of protecting groups and the removal of protecting groups in a sequential manner utilizing suitable protecting groups such as those described in *Protecting Groups in Organic Synthesis* by T. Greene is well known and appreciated by those skilled in the art. The removal of protecting groups or the removal of protecting groups in a sequential manner as required gives disulfides of Formula (I).

The following examples present typical syntheses as described in Scheme 1. These examples are understood to be illustrative only and are not intended to limit the scope of the invention in any way. As used in the following examples, the following terms have the meanings indicated: "g" refers to grams, "mmol" refers to millimoles, "mL" refers to milliliters, "°C." refers to degrees Celsius, "$R_f$" refers to retention factor, "mp" refers to melting point, "dec" refers to decomposition, "M" refers to molar, and "TLC" refers to thin layer chromatography.

PREPARATION 1

2-[4-(2-Mercapto-3-phenyl-propionyl-amino)-3-oxo-1,3,4,5-tetrahydro-benzo[c]azepin-2-yl]-4-methyl-valeric acid, tert-butyl ester Combine 2-[4-(2-Benzoylsulfanyl-3-phenyl-propionyl-amino)-3-oxo-1,3,4,5-tetrahydro-benzo[c]azepin-2-yl]-4-methyl-valeric acid, tert-butyl ester (0.229 mmol) in degassed methanol (3 mL) and cool in an ice bath. Treat with degassed 1N aqueous lithium hydroxide (1.0 mL) and stir, allowing the ice bath to warm gradually over 3 hours. With the reaction at 0° C., acidify with 5% hydrochloric acid. Partition between methylene chloride and water, dry ($Na_2SO_4$) and purify by silica gel chromatography to give the title compound.

EXAMPLE 1

2-[4-(2-Thio-3-phenyl-propionyl-amino)-3-oxo-1,3,4,5-tetrahydro-benzo[c]azepin-2-yl]-4-methyl-valeric acid, tert-butyl ester, (S)-N-(t-butoxycarbonyl)-1-(2-methylpropyl)-2-(thio)-ethylamine, disulfide Scheme 1, step a Combine 2-[4-(2-Mercapto-3-phenyl-propionyl-amino)-3-oxo-1,3,4,5-tetrahydro-benzo[c]azepin-2-yl]-4-methyl-valeric acid, tert-butyl ester (1.20 mmol) and (S)-N-(t-butoxycarbonyl)-1-(2-methylpropyl)-2-(thio)-ethylamine, 2-thiopyridine, disulfide (1.46 mmol) in degassed ethanol (10 mL). Stir for 20 hours. Evaporate in vacuo. Chromatograph on silica gel to give the title compound.

EXAMPLE 2

2-[4-(2-Thio-3-phenyl-propionyl-amino)-3-oxo-1,3,4,5-tetrahydro-benzo[c]azepin-2-yl]-4-methyl-valeric acid, tert-butyl ester, (R)-N-(t-butoxycarbonyl)-1-(2-methylpropyl)-2-(thio)-ethylamine, disulfide Scheme 1, step a Combine 2-[4-(2-Mercapto-3-phenyl-propionyl-amino)-3-oxo-1,3,4,5-tetrahydro-benzo[c]azepin-2-yl]-4-methyl-valeric acid, tert-butyl ester and (R)-N-(t-butoxycarbonyl)-1-(2-methylpropyl)-2-(thio)-ethylamine, 2-thiopyridine, disulfide (1.46 mmol) in degassed ethanol (10 mL). Stir for 18 hours. Evaporate in vacuo. Chromatograph on silica gel to give the title compound.

EXAMPLE 3

2-[4-(2-Thio-3-phenyl-propionyl-amino)-3-oxo-1,3,4,5-tetrahydro-benzo[c]azepin-2-yl]-4-methyl-valeric acid, (S)-N-1-(2-methylpropyl)-2-(thio)-ethylamine, disulfide Scheme 1, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, (S)-N-(t-butoxycarbonyl)-1-(2-methylpropyl)-2-(thio)-ethylamine, disulfide (1.00 mmol) with methylene chloride (5 mL) and treat with anisole (1.50 mL) then with trifluoroacetic acid (1.0 mL). Stir at room temperature for 15 hours, partition between ethyl acetate and brine. Wash the organic layer with brine, dry ($Na_2SO_4$) and purify by silica gel chromatography to give the title compound.

EXAMPLE 4

2-[4-(2-Thio-3-phenyl-propionyl-amino)-1,3,4,5-tetrahydro-benzo[c]azepin-2-yl]-4-methyl-valeric acid, (R)-1-(2-methylpropyl)-2-(thio)-ethylamine, disulfide Scheme 1, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, (R)-N-(t-butoxycarbonyl)-1-(2-methylpropyl)-2-(thio)-ethylamine, disulfide (1.2 mmol) with methylene chloride (5 mL) and treat with anisole (1.20 mL) then with trifluoroacetic acid (1.0 mL). Stir at room temperature for 15 hours, partition between ethyl acetate and brine. Wash the organic layer with brine, dry ($Na_2SO_4$) and purify by silica gel chromatography to give the title compound.

EXAMPLE 5

2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thiopyridine, disulfide Combine 2-[4-(2-Thio-3-phenyl-propionyl-amino)-3-oxo-1,3,4,5-tetrahydro-benzo[c]azepin-2-yl]-4-methyl-valeric acid, tert-butyl ester (4.0 mmol) and 2,2'-dithiodipyridine (16.0 mmol) is degassed ethanol (24 mL) and dichloromethane (6 mL). Stir under an inert atmosphere at ambient temperature for 20 hours. Evaporate in vacuo to obtain a residue. Chromatograph the residue on silica gel to give the title compound.

An alternate general synthetic procedure is set forth in Scheme 2 for preparing compounds of Formula (I). In Scheme 2, all substituents unless otherwise indicated, are as previously defined. Starting materials, reagents, techniques, and procedures used in Scheme 2 are well known and appreciated by one of ordinary skill in the art.

SCHEME 2

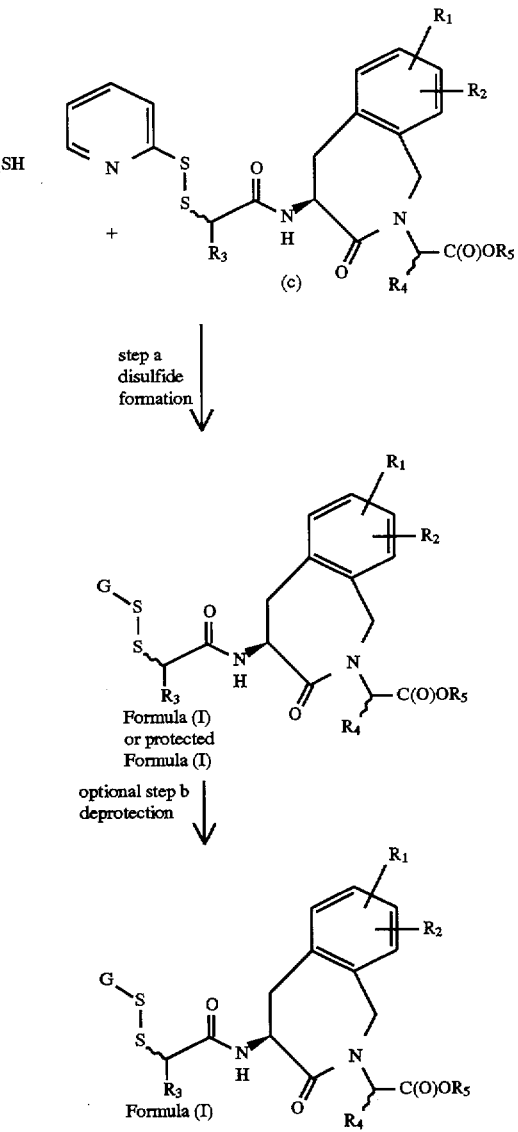

In Scheme 2, step a, an appropriate thiol of structure (d) is contacted with an appropriate disulfide of structure (4) to give a disulfide of Formula (I) or a protected disulfide of Formula (I) by the method taught above in Scheme A, step a. An appropriate thiol of structure (d) is one in which G is as desired in the final product of Formula (I) or gives rise after deprotection to G as desired in the final product of Formula (I). An appropriate disulfide of the structure (c) is one in which $R_1$, $R_2$, $R_3$, $R_4$ and $R_5$ are as desired in the final product of Formula (I) or give rise after deprotection to $R_1$, $R_2$, $R_3$, $R_4$ and $R_5$ as desired in the final product of Formula (I). An appropriate compound of structure (c) can be prepared by methods known analogously in the art, B. P. Roques et al, *J. Med. Chem.* 33, 2473–2481 (1992), from compounds of structure (a) prepared according to Scheme A.

In Scheme 2, optional step b, a protected disulfide of Formula (I) is deprotected to give a disulfide of Formula (I) as taught in Scheme 1 optional, step b above.

The following examples present typical syntheses as described in Scheme 2. These examples are understood to be illustrative only and are not intended to limit the scope of the invention in any way. As used in the following examples, the following terms have the meanings indicated: "g" refers to grams, "mmol" refers to millimoles, "mL" refers to milliliters, "°C." refers to degrees Celsius, "$R_f$" refers to retention factor, "mp" refers to melting point, "dec" refers to decomposition, "M" refers to molar, and "TLC" refers to thin layer chromatography.

EXAMPLE 6

2-[4-(2-Thio-3-phenyl-propionyl-amino)-3-oxo-1,3, 4,5-tetrahydro-benzo[c]azepin-2-yl]-4-methyl-valeric acid, tert-butyl ester, N-(t-butoxycarbonyl)-L-cysteine ethyl ester, disulfide Scheme 2, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thiopyridine, disulfide (1.4 mmol) and N-(t-butoxycarbonyl)-L-cysteine ethyl ester (2.0 mmol) in degassed ethanol/dichloromethane (10 mL)/(2 mL). Stir for 18 hours. Evaporate in vacuo to obtain a residue. Chromatograph the residue on silica gel to give the title compound.

EXAMPLE 7

2-[4-(2-Thio-3-phenyl-propionyl-amino)-3-oxo-1,3, 4,5-tetrahydro-benzo[c]azepin-2-yl]-4-methyl-valeric acid, tert-butyl ester, benzylthio, disulfide Scheme 2, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thiopyridine, disulfide (1.4 mmol) and benzylthiol (1.7 mmol) in degassed ethanol/dichloromethane (15 mL)/(3 mL). Stir for 18 hours. Add benzylthiol (1.7 mmol) and stir for 24 hours. Evaporate in vacuo to obtain a residue. Chromatograph the residue on silica gel to give the title compound.

EXAMPLE 8

2-[4-(2-Thio-3-phenyl-propionyl-amino)-3-oxo-1,3, 4,5-tetrahydro-benzo[c]azepin-2-yl]-4-methyl-valeric acid, tert-butyl ester, ethylthio, disulfide Scheme 2, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thiopyridine, disulfide (1.68 mmol) and ethylthiol (2.7 mmol) in degassed ethanol/dichloromethane (15 mL)/(3 mL). Stir for 18 hours. Add ethylthiol (2.7 mmol) and stir for 24 hours. Evaporate in vacuo to obtain a residue. Chromatograph the residue on silica gel eluting 30% ethyl acetate/hexane to give the title compound as a solid.

EXAMPLE 9

2-[4-(2-Thio-3-phenyl-propionyl-amino)-3oxo-1,3,4, 5-tetrahydro-benzo[c]azepin-2-yl]-4-methyl-valeric acid, tert-butyl ester, disulfide, 2-hydroxyethylthio, disulfide Scheme 2, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thiopyridine, disulfide (1.54 mmol) and 2-hydroxyethylthiol (2.85 mmol) in degassed ethanol/dichloromethane (15 mL)/(3 mL). Stir for 18 hours. Dilute with dichloromethane and extract with saturated sodium chloride solution. Dry the organic layer over $MgSO_4$, filter, and concentrate in vacuo to obtain a residue. Chromatograph the residue on silica gel to give the title compound.

EXAMPLE 10

2-[4-(2-Thio-3-phenyl-propionyl-amino)-3-oxo-1,3, 4,5-tetrahydro-benzo[c]azepin-2-yl]-4-methyl-valeric acid, tert-butyl ester, 2-pyridylmethylthio, disulfide Scheme 2, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thiopyridine, disulfide (1.40 mmol) and pyridylmethylthiol (2.10 mmol) in degassed ethanol/dichloromethane (10 mL)/(2 mL). Stir for 18 hours. Concentrate in vacuo to obtain a residue. Chromatograph the residue on silica gel to give the title compound.

PREPARATION 2

2-Thiolacetic acid morpholine carboxamide

Preparation of starting material for Scheme 2, step a

Combine chloroacetyl chloride (2.00 mL, 25.0 mmol) and N-methylmorpholine (2.76 mL, 25.0 mmol) in dichloromethane (100 mL). Cool in an ice-bath. Add morpholine (2.19 mL, 25.0 mmol) and stir in the ice-bath for 1 hour. Warm to ambient temperature and stir for 1 hour. Extract with cold aqueous 5% sulfuric acid solution, saturated aqueous sodium bicarbonate solution, and saturated aqueous sodium chloride solution. Dry the organic layer over $Na_2SO_4$, filter, and evaporate in vacuo to obtain chloroacetic acid morpholine carboxamide.

Combine chloroacetic acid morpholine carboxamide prepared above (2.88 g, 17.6 mmol) and thiolacetic acid (1.40 mL, 20.0 mmol) in degassed dimethylformamide (10 mL). Slowly add cesium carbonate (3.26 g, 10.0 mmol) providing cooling as needed to keep the temperature of the reaction mixture below 40° C. Stir at ambient temperature for 16 hours. Partition the reaction mixture between water and ethyl acetate. Dry the organic layer over $Na_2SO_4$, filter, and evaporate in vacuo to obtain a residue. Chromatograph the residue on silica gel eluting sequentially with 40% ethyl acetate/hexane and then 66% ethyl acetate/hexane to give 2-acetylthioacetic acid morpholine carboxamide.

Combine 2-acetylthioacetic acid morpholine carboxamide obtained above (2.50 g, 12.0 mmol) and degassed methanol (50 mL). Cool in an ice-bath. Add lithium hydroxide hydrate (1.0 g,24.0 mmol). Stir for 3 hours. Acidify the reaction mixture to pH=1 with 6M hydrochloric acid solution. Partition the reaction mixture between water and dichloromethane. Extract the organic layer with saturated aqueous ammonium chloride solution. Dry the organic layer over $Na_2SO_4$, filter, and evaporate in vacuo to obtain a residue. Chromatograph the residue on silica gel eluting with ethyl acetate to give the title compound.

EXAMPLE 11

2-[4-(2-Thio-3-phenyl-propionyl-amino)-3-oxo-1,3, 4,5-tetrahydro-benzo[c]azepin-2-yl]-4-methyl-valeric acid, tert-butyl ester, 2-thioacetic acid morpholine carboxamide Scheme 2, step a Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thiopyridine, disulfide (1.40 mmol) and 2-thiolacetic acid morpholine carboxamide (2.0 mmol) in degassed ethanol/dichloromethane (10 mL)/(2 mL). Stir for 16 hours. Concentrate in vacuo to obtain a residue. Chromatograph the residue on silica gel eluting with 50% ethyl acetate/dichloromethane to give the title compound.

EXAMPLE 12

2-[4-(2-Thio-3-phenyl-propionyl-amino)-3-oxo-1,3, 4,5-tetrahydro-benzo[c]azepin-2-yl]-4-methyl-valeric acid, L-cysteine ethyl ester, disulfide trifluoroacetic acid salt Scheme 2, optional step b Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, N-(t-butoxycarbonyl)-L-cysteine ethyl ester, disulfide (1.20 mmol) anisole (13.0 mmol) and dichloromethane (15 mL). Cool in an ice-bath. Add trifluoroacetic acid (3 mL). Stir for 2 hours in the ice-bath and thee warm to ambient temperature and stir an additional 2 hours. Evaporate in vacuo to obtain a residue. Add carbon tetrachloride to the residue and evaporate in vacuo to obtain a residue. Triturate with hexane, filter and dry in vacuo to give the title compound.

EXAMPLE 13

2-[4-(2-Thio-3-phenyl-propionyl-amino)-3-oxo-1,3, 4,5-tetrahydro-benzo[c]azepin-2-yl]-4-methyl-valeric acid, benzylthio, disulfide Scheme 2, optional step b Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, benzylthio, disulfide (1.02 mmol) anisole (10.0 mmol) and dichloromethane (10 mL). Cool in an ice-bath. Add trifluoroacetic acid (2.0 mL). Stir for 2.5 hours in the ice-bath. Evaporate in vacuo to obtain a residue. Dissolve the residue in diethyl ether and extract with 1M hydrochloric acid solution. Extract the aqueous layer with dichloromethane. Combine the organic layers, dry over $MgSO_4$, filter and concentrate in vacuo to obtain a residue. Chromatograph the residue on silica gel to give the title.

EXAMPLE 14

2-[4-(2-Thio-3-phenyl-propionyl-amino)-3-oxo-1,3, 4,5-tetrahydro-benzo[c]azepin-2-yl]-4-methyl-valeric acid, ethylthio, disulfide Scheme 2, optional step b Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, ethylthio, disulfide (1.43 mmol) anisole (10.0 mmol) and dichloromethane (14 mL). Cool in an ice-bath. Add trifluoroacetic acid (2.0 mL). Stir for 2.5 hours in the ice-bath. Evaporate in vacuo to obtain a residue. Chromatograph the residue on silica gel to give the title compound.

EXAMPLE 15

2-[4-(2-Thio-3-phenyl-propionyl-amino)-3-oxo-1,3, 4,5-tetrahydro-benzo[c]azepin-2-yl]-4-methyl-valeric acid, 2-hydroxyethylthio, disulfide Scheme 2, optional step b Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, disulfide, 2-hydroxyethylthio, disulfide (0.9 mmol) anisole (10.0 mmol) and dichloromethane (10 mL). Cool in an ice-bath. Add trifluoroacetic acid (2.0 mL). Stir for 2.5 hours in the ice-bath. Evaporate in vacuo to obtain a residue. Chromatograph the residue on silica gel to give the title compound.

EXAMPLE 16

2-[4-(2-Thio-3-phenyl-propionyl-amino)-3-oxo-1,3, 4,5-tetrahydro-benzo[c]azepin-2-yl]-4-methyl-valeric acid, 2-pyridylmethylthio, disulfide trifluoroacetic acid salt Scheme 2, optional step b Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-pyridylmethylthio, disulfide (0.5 mmol) anisole (6.9 mmol) and dichloromethane (15 mL). Cool in an ice-bath. Add trifluoroacetic acid (1.4 mL). Stir for 3 hours in the ice-bath. Evaporate in vacuo to obtain a residue. Add carbon tetrachloride to the residue and evaporate in vacuo to obtain a residue. Triturate with hexane, filter and dry to give the title compound.

EXAMPLE 17

2-[4-(2-Thio-3-phenyl-propionyl-amino)-3-oxo-1,3, 4,5-tetrahydro-benzo[c]azepin-2-yl]-4-methyl-valeric acid, 2-thioacetic acid morpholine carboxamide, disulfide Scheme 2, Optional step b Combine 2-[4-(2-Thio-3-phenyl-propionyl-amino)-3-oxo-1,3,4,5-tetrahydro-benzo[c]azepin-2-yl]-4-methyl-valeric acid, tert-butyl ester, 2-thioacetic acid morpholine carboxamide, disulfide (0.68 mmol) anisole (6.9 mmol) and dichloromethane (7.5 mL). Cool in an ice-bath. Add trifluoroacetic acid (2.0 mL). Stir for 2 hours in the ice-bath. Evaporate in vacuo to obtain a residue. Chromatograph the residue on silica gel to give the title compound.

The compounds of structure (a) can be prepared by utilizing procedures and techniques well known and appreciated by one of ordinary skill in the art. A general synthetic scheme for preparing these compounds is set forth in Scheme A wherein all substituents, unless otherwise indicated, are previously defined.

Scheme A
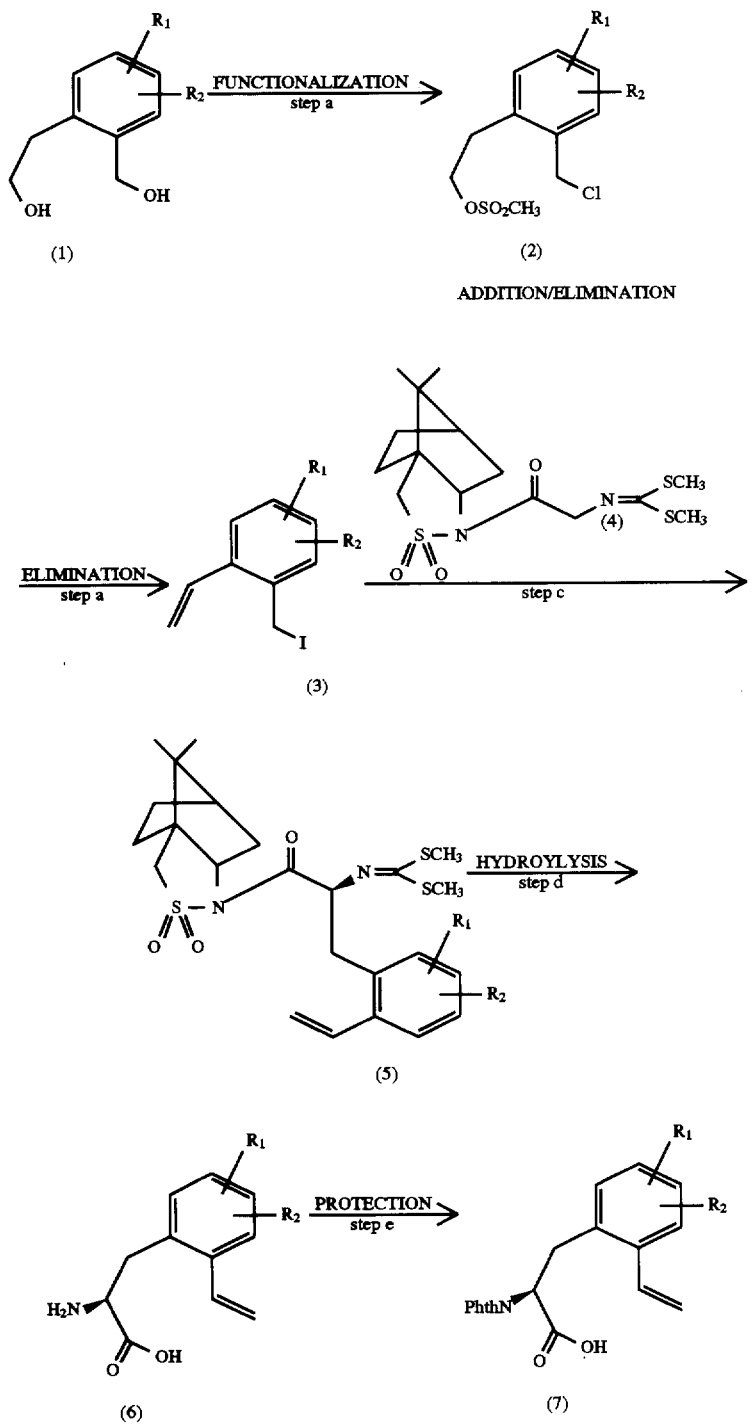

-continued
Scheme A
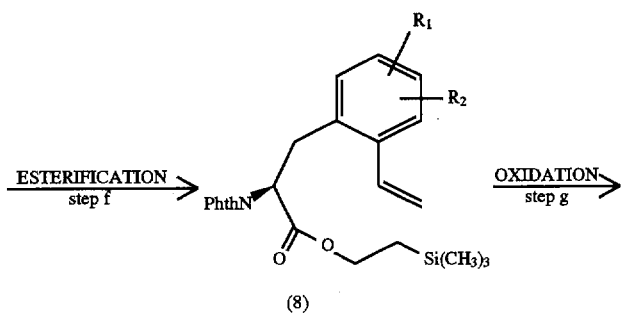
REDUCTION AMINATION
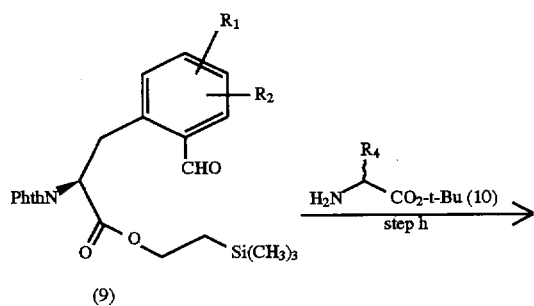
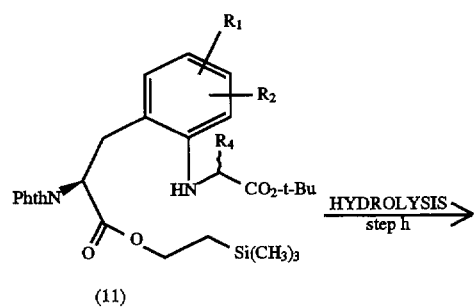
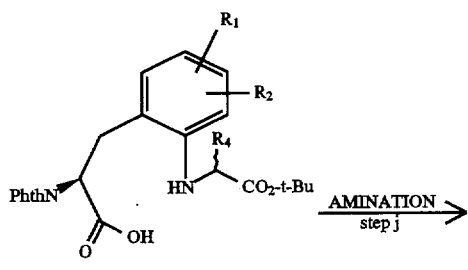

-continued
Scheme A

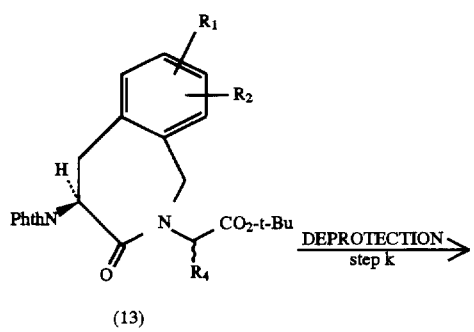

(13)

AMINATION

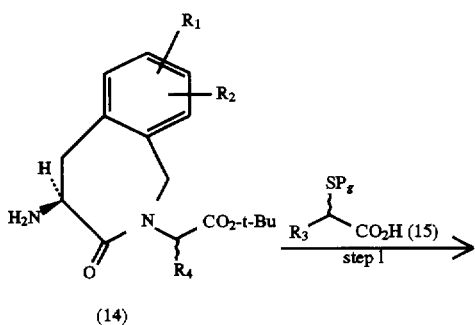

(14)

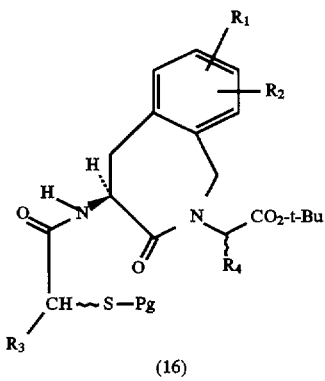

(16)

Pg = acetyl or benzoyl

In step a, an appropriate 2-(2-hydroxymethyl-phenyl)-ehtanol derivative of structure (1) is functionalized to give the corresponding methanesulfonic acid 2-(2-chloromethyl-phenyl)-ethyl ester derivative of structure (2).

For example, an appropriate 2-(2-hydroxymethyl-phenyl)-ethanol derivative of structure (1) is treated initially with lithium chloride and a suitable non-nucleophilic base, such as collidine in a suitable aprotic organic solvent such as dimethylformamide. This is followed by treatment with a suitable mesylating agent, such as mesyl chloride. The reaction is typically conducted at a temperature range of from −30° to room temperature, preferably 0° C. and for a period of time ranging from 2–10 hours. The corresponding methanesulfonic acid 2-(2-chloromethyl-phenyl)-ethyl ester derivative of structure (2) is recovered from the reaction mixture by extractive methods as are known in the art and may be purified by chromatography.

In step b, the methanesulfonate functionality of the appropriate methanesulfonic acid 2-(2-chloromethyl-phenyl)-ethyl ester derivative of structure (2) is eliminated and the chloro substituted with iodo to give the corresponding 1-iodomethyl-2-vinyl-benzene derivative of structure (3).

For example, the appropriate methanesulfonic acid 2-(2-chloromethyl-phenyl)-ethyl ester derivative of structure (2) is treated with a suitable non-nucleophilic base, such as potassium tert-butoxide in a suitable aprotic organic solvent, such as diethyl ether. The reaction is typically conducted at a temperature range of form −30° C. to room temperature, preferably 0° C. and for a period of time ranging from 15 minutes to 5 hours. The corresponding 1-chloromethyl-2-vinyl-benzene derivative is recovered from the reaction mixture by extractive methods as are known in the art.

The appropriate 1-chloromethyl-2-vinyl-benzene derivative is then treated with a suitable iodinating agent, such as sodium iodide, in a suitable solvent, such as acetone. The reaction is conducted at a temperature range of from room temperature to reflux temperature of the solvent and for a period of time ranging from 15 minutes to 5 hours. The corresponding corresponding 1-iodomethyl-2-vinyl-benzene derivative of structure (3) is recovered from the reaction mixture by extractive methods as are known in the art.

In step c, the appropriate 1-iodomethyl-2-vinyl-benzene derivative of structure (3) is subjected to an addition, elimination reaction with 2-(bis-methylsulfonyl-methyleneamino)-1-(10,10-dimethyl-3,3-dioxo-3-thia-4-aza-tricyclo[5.2.1.0 1,5]dec-4-yl)-ethanone (4) to give the corresponding 2-(bis-methylsulfonyl-methyleneamino)-1-(10,10-dimethyl-3,3-dioxo-3-thia-4-aza-tricyclo[5.2.1.0 1,5]dec-4-yl)-3-(2-vinyl-phenyl)-propan-1-one derivative of structure (5).

For example, the anion of 2-(bis-methylsulfonyl-methyleneamino)-1-(10,10-dimethyl-3,3-dioxo-3-thia-4-aza-tricyclo[5.2.1.0 1,5]dec-4-yl)-ethanone (4) is formed by treating 2-(bis-methylsulfonyl-methyleneamino)-1-(10,10-dimethyl-3,3-dioxo-3-thia-4-aza-tricyclo[5.2.1.0 1,5]dec-4-yl)-ethanone (4) with a suitable non-nucleophilic base, such as n-butyllithium in a suitable aprotic organic solvent, such as tetrahydrofuran. The reaction is conducted at a temperature range of from −78° C. to −30° C., preferable −78° C. and for a period of time ranging from 30 minutes to 5 hours. The appropriate 1-iodomethyl-2-vinyl-benzene derivative of structure (3) is then added and the reaction is conducted at a temperature range of from −78° C. to room temperature for a period of time ranging from 1–24 hours. The corresponding 2-(bis-methylsulfonyl-methyleneamino)-1-(10,10-dimethyl-3,3-dioxo-3-thia-4-aza-tricyclo[5.2.1.0 1,5]dec-4-yl)-3-(2-vinyl-phenyl)-propan-1-one derivative of structure (5) is recovered from the reaction mixture by extractive methods as are known in the art and may be purified by chromatography.

In step d, the appropriate 2-(bis-methylsulfonyl-methyleneamino)-1-(10,10-dimethyl-3,3-dioxo-3-thia-4-aza-tricyclo[5.2.1.0 1,5]dec-4-yl)-3-(2-vinyl-phenyl)-propan-1-one derivative of structure (5) is hydrolyzed to give the corresponding 2-amino-3-(2-vinyl-phenyl)-propionic acid derivative of structure (6).

For example, the appropriate 2-(bis-methylsulfonyl-methyleneamino)-1-(10,10-dimethyl-3,3-dioxo-3-thia-4-aza-tricyclo[5.2.1.0 1,5]dec-4-yl)-3-(2-vinyl-phenyl)-propan-1-one derivative of structure (5) is treated with a suitable acid such as aqueous hydrochloric acid in a suitable organic solvent such as tetrahydrofuran. The reaction is conducted at a temperature range of from −10° C. to room temperature and for a period of time ranging from 30 minutes to 20 hours. Evaporation of the solvent followed by treatment with inorganic base such as aqueous lithium hydroxide in a suitable organic solvent, such as tetrahydrofuran. The reaction is conducted at a temperature range of from −10° C. to room temperature and for a period of time ranging from 30 minutes to 10 hours. After acidification, the corresponding 2-amino-3-(2-vinyl-phenyl)-propionic acid derivative of structure (6) was isolated by evaporation of solvents.

In step e, the amino functionality of the appropriate 2-amino-3-(2-vinyl-phenyl)-propionic acid derivative of structure (6) is protected to give the corresponding 2-(1,3-dioxo-1,3-dihydro-isoindol-2-yl)-3-(2-vinyl-phenyl)-propionic acid derivative of structure (7).

For example, the appropriate 2-amino-3-(2-vinyl-phenyl)-propionic acid derivative of structure (6) is treated with an appropriate phthalimide protecting agent, such as N-carbethoxyphthalimide in the presence of a suitable non-nucleophilic base, such as aqueous sodium carbonate. The reaction is conducted at a temperature range of from −10° C. to room temperature and for a period of time ranging from 1– 10 hours. The corresponding 2-(1,3-dioxo-1,3-dihydro-isoindol-2-yl)-3-(2-vinyl-phenyl)-propionic acid derivative of structure (7) is recovered from the reaction zone by extractive methods as are known in the art and may be purified by chromatography.

In step f, the carboxylic acid functionality of the appropriate 2-(1,3-dioxo-1,3-dihydro-isoindol-2-yl)-3-(2-vinyl-phenyl)-propionic acid derivative of structure (7) is esterified to give the corresponding 2-(1,3-dioxo-1,3-dihydro-isoindol-2-yl)-3-(2-vinyl-phenyl)-propionic acid, 2-trimethylsilanyl-ethyl ester derivative of structure (8).

For example, the appropriate 2-(1,3-dioxo-1,3-dihydro-isoindol-2-yl)-3-(2-vinyl-phenyl)-propionic acid derivative of structure (7) is treated with 2-(trimethylsilyl)ethanol in the presence of a suitable non-nucleophilic base, such as pyridine, in a suitable organic solvent, such as tetrahydrofuran. The reaction is conducted at a temperature range of from −30° C. to room temperature and for a period of time ranging from 5 minutes to 2 hours. A coupling agent, such as 1-(3-dimethylaminopropyl)-3-ethylcarbodiimide (EDC) is then added and the reaction conducted at a temperature range of from −30° C. to room temperature for a period of time ranging from 10–48 hours. The corresponding 2-(1,3-dioxo-1,3-dihydro-isoindol-2-yl)-3-(2-vinyl-phenyl)-propionic acid, 2-trimethylsilanyl-ethyl ester derivative of structure (8) recovered from the reaction zone by extractive methods as are known in the art and may be purified by chromatography.

In step g, the vinyl functionality of the appropriate 2-(1,3-dioxo-1,3-dihydro-isoindol-2-yl)-3-(2-vinyl-phenyl)-propionic acid, 2-trimethylsilanyl-ethyl ester derivative of structure (8) is oxidized to give the corresponding 2-(1,3-dioxo-1,3-dihydro-isoindol-2-yl)-3-(2-formyl-phenyl)-propionic acid, 2-trimethylsilanyl-ethyl ester derivative of structure (9).

For example, the appropriate 2-(1,3-dioxo-1,3-dihydro-isoindol-2-yl)-3-(2-vinyl-phenyl)-propionic acid, 2-trimethylsilanyl-ethyl ester derivative of structure (8) is treated with ozone in a suitable organic solvent such as methylene chloride and methanol. The reaction is conducted at a temperature range of from −78° C. to −50° C. and for a period of time necessary for a blue color to persist. After purging the reaction with nitrogen and quenching by methods known in the art, such as addition of dimethylsulfide and pyridine, the corresponding 2-(1,3-dioxo-1,3-dihydro-isoindol-2-yl)-3-(2-formyl-phenyl)-propionic acid, 2-trimethylsilanyl-ethyl ester derivative of structure (9) is recovered from the reaction zone by extractive methods as are known in the art and may be purified by chromatography.

In step h, the appropriate 2-(1,3-dioxo-1,3-dihydro-isoindol-2-yl)-3-(2-formyl-phenyl)-propionic acid, 2-trimethylsilanyl-ethyl ester derivative of structure (9) is subjected to reductive amination with an appropriate amino acid, tert-butyl ester derivative of structure (10) to give the corresponding 2-{2-[2-(1,3-dioxo-1,3-dihydro-isoindol-2-yl)-2-(2-trimethylsilanyl-ethoxycarbonyl)-ethyl]-benzylamino}-acetic acid, tert-butyl ester derivative of structure (11).

For example, the appropriate 2-(1,3-dioxo-1,3-dihydro-isoindol-2-yl)-3-(2-formyl-phenyl)-propionic acid, 2-trimethylsilanyl-ethyl ester derivative of structure (9) is treated with an appropriate amino acid, tert-butyl ester derivative of structure (10) in an appropriate polar organic solvent, such as methanol under dehydrating conditions, such as molecular sieves. The reaction is conducted at a temperature ranged of from −10° C. to reflux temperature of the solvent, preferably room temperature, and for a period of time ranging from 30 minutes to 10 hours. A suitable reducing agent, such as sodium cyanoborohydride, is then added and the reaction is conducted at a temperature range of from −10° to reflux temperature of the solvent, preferably room temperature, and for a period of time ranging from 30 minutes to 24 hours. The corresponding 2-{2-[2-(1,3-dioxo-1,3-dihydro-isoindol-2-yl)-2-(2-trimethylsilanyl-ethoxycarbonyl)-ethyl]-benzylamino}-acetic acid, tert-butyl ester derivative of structure (11) is recovered from the reaction zone by extractive methods as are known in art and may be purified by chromatography.

As one skill in the art would realize, those amino acid, tert-butyl ester derivatives of structure (10) wherein R$_4$ has a reactive functionality, the reactive functionality may be protected prior to the reductive amination reaction of step h. The selection and utilization of suitable protecting groups is well known by one of ordinary skill in the art and is described in "*Protective Groups in Organic Synthesis*", Theodora W. Greene, Wiley (1981).

In step i, the ester functionality of the appropriate 2-{2-[2-(1,3-dioxo-1,3-dihydro-isoindol-2-yl)-2-(2-trimethylsilanyl-ethoxycarbonyl)-ethyl]-benzylamino}-acetic acid, tert-butyl ester derivative of structure (11) is hydrolyzed to give the corresponding 2-{2-[2-(1,3-dioxo-1,3-dihydro-isoindol-2-yl)-ethyl]-benzylamino}-acetic acid, tert-butyl ester derivative of structure (12).

For example, the appropriate 2-{2-[2-(1,3-dioxo-1,3-dihydro-isoindol-2-yl)-2-(2-trimethylsilanyl-ethoxycarbonyl)-ethyl]-benzylamino}-acetic acid, tert-butyl ester derivative of structure (11) is treated with an appropriate fluoride reagent, such as tetrabutylammonium fluoride in a suitable organic solvent, such as tetrahydrofuran. The reaction is conducted at a temperature range of from −10° C. to room temperature and for a period of time ranging from 30 minutes to 5 hours. The corresponding 2-{2-[2-(1,3-dioxo-1,3-dihydro-isoindol-2-yl)-ethyl]-benzylamino}-acetic acid, tert-butyl ester derivative of structure (12) is recovered from the reaction zone by extractive methods as are known in art and may be purified by chromatography.

In step j, the appropriate 2-(2-[2-(1,3-dioxo-1,3-dihydro-isoindol-2-yl)-ethyl]-benzylamino)-acetic acid, tert-butyl ester derivative of structure (12) is subjected to a ring closure amination reaction to give the corresponding 2-[4-(1,3-dioxo-1,3-dihydro-isoindol-2-yl)-3-oxo-1,3,4,5-tetrahydro-benzo[c]azepin-2-yl]-acetic acid, tert-butyl ester derivative of structure (13).

For example, the appropriate 2-{2-[2-(1,3-dioxo-1,3-dihydro-isoindol-2-yl)-ethyl]-benzylamino}-acetic acid, tert-butyl ester derivative of structure (12) is treated with a suitable activating agent, such as isobutylchloroformate, in the presence of a suitable non-nucleophilic base, such as N-methylmorpholine in a suitable organic solvent, such as tetrahydrofuran. The reaction is conducted at a temperature range of from −10° C. to reflux temperature of the solvent and for a period of time ranging from 30 minutes to 10 hours. The corresponding 2-[4-(1,3-dioxo-1,3-dihydro-isoindol-2-yl)-3-oxo-1,3,4,5-tetrahydro-benzo[c]azepin-2-yl]-acetic acid, tert-butyl ester derivative of structure (13) is recovered from the reaction zone by evaporation and may be purified by chromatography.

In step k, the phthalimide protecting group of the appropriate 2-[4-(1,3-dioxo-1,3-dihydro-isoindol-2-yl)-3-oxo-1,3,4,5-tetrahydro-benzo[c]azepin-2-yl]-acetic acid, tert-butyl ester derivative of structure (13) is removed to give the corresponding 2-(4-amino-3-oxo-1,3,4,5-tetrahydro-benzo[c]azepin-2-yl)-acetic acid, tert-butyl ester derivative of structure (14).

For example, the phthalimide protecting groups of the appropriate can be removed using hydrazine monohydrate in a suitable protic solvent such as methanol. The reaction is conducted at a temperature range of from −10° C. to room temperature and for a period of time ranging from 2 hours to 4 days. The corresponding 2-(4-amino-3-oxo-1,3,4,5-tetrahydro-benzo[c]azepin-2-yl)-acetic acid, tert-butyl ester derivative of structure (14) is recovered from the reaction zone by filtration and evaporation.

In step 1, the appropriate 2-(4-amino-3-oxo-1,3,4,5-tetrahydro-benzo[c]azepin-2-yl)-acetic acid, tert-butyl ester derivative of structure (14) is subjected to an amination reaction with the appropriate thioacetate or thiobenzoate derivative of structure (15) to give the corresponding 2-[4-(2-acetylsulfanyl-3-phenyl-propionyl-amino)-3-oxo-1,3,4,5-tetrahydro-benzo[c]azepin-2-yl]-acetic acid, tert-butyl ester derivative or the corresponding 2-[4-(2-benzoylsulfanyl-3-phenyl-propionyl-amino)-3-oxo-1,3,4,5-tetrahydro-benzo[c]azepin-2-yl]-acetic acid, tert-butyl ester derivative of structure (16).

For example, the appropriate 2-(4-amino-3-oxo-1,3,4,5-tetrahydro-benzo[c]azepin-2-yl)-acetic acid, tert-butyl ester derivative of structure (14) can be reacted with the appropriate thioacetate or thiobenzoate derivative of structure (15) in the presence of a coupling reagent such ad EEDQ (1-ethoxycarbonyl-2-ethoxy-1,2-dihydroquinoline), DCC (1,3-dicyclohexylcarbodiiminde), or diethylcyanophosponate in a suitable aprotic solvent such as methylene chloride. The reaction is conducted at a temperature range of from −10° C. to room temperature and for a period of time ranging from 1 hour to 2 days. The corresponding 2-[4-(2-benzoylsulfanyl-3-phenyl-propionyl-amino)-3-oxo-1,3,4,5-tetrahydro-benzo[c]azepin-2-yl]-acetic acid, tert-butyl ester derivative of structure (16) is recovered from the reaction zone by extractive methods as are known in the art and may be purified by chromatography.

As one skill in the art would realize, those 2-[4-(2-acetylsulfanyl-3-phenyl-propionyl-amino)-3-oxo-1,3,4,5-tetrahydro-benzo[c]azepin-2-yl]-acetic acid, tert-butyl ester derivative or 2-[4-(2-benzoylsulfanyl-3-phenyl-propionyl-amino)-3-oxo-1,3,4,5-tetrahydro-benzo[c]azepin-2-yl]-acetic acid, tert-butyl ester derivatives of structure (16) wherein Pg is an acetyl or benzoyl protective group can be hydrolyzed using techniques and procedure well known in the art to give compounds of structure (a). The selection and utilization of suitable deprotecting agents is well known by one of ordinary skill in the art and is described in "*Protective Groups in Organic Synthesis*", Theodora W. Greene, Wiley (1981).

For example, thioacetate or thiobenzoate functionality of the appropriate thioacetate or thiobenzoate compound of structure (a) in which R$_5$ is t-butyl can be removed with lithium hydroxide in a suitable solvent mixture such as tetrahydrofuran and ethanol to give the appropriate thio compound of structure (a) used as starting material in Scheme 1.

The t-butyl ester functionality of the appropriate thioacetate or thiobenzoate compound of structure (a) in which R$_5$ is t-butyl can be removed using trifluoroacetic acid to give the appropriate thioacetate or thiobenzoate carboxylic acid compound of structure (a) in which R$_5$ is hydrogen.

Alternatively, the carboxylic acid functionality of the appropriate thioacetate or thiobenzoate carboxylic acid compound of structure (a) can be re-esterified using techniques and procedures well known and appreciated in the art. For example, a thioacetate or thiobenzoate compound of structure (a) in which R$_5$ is a C$_1$–C$_4$ alkyl or an Ar—Y— group, or —CH$_2$O—C(O)C(CH$_3$)$_3$ can be prepared by treating the thioacetate or thiobenzoate carboxylic acid compound of structure (a) in which R$_5$ is hydrogen with the appropriate C$_1$–C$_4$ alkyl halide, Ar—Y halide or chloromethyl pivalate in a suitable aprotic solvent, such as dimethylformamide along with a non-nucleophilic base, such as cesium carbonate.

The thioacetate or thiobenzoate functionalities of the appropriate thioacetate or thiobenzoate compound of structure (a) in which $R_5$ is a $C_1$-$C_4$ alkyl or an Ar—Y— group, or —$CH_2O$—$C(O)C(CH_3)_3$ can be hydrolyzed to the corresponding thiol compounds of structure (a) with ammonia in a suitable protic solvent, such as methanol.

Starting materials for use in the general synthetic procedures outlined in Scheme A are readily available to one of ordinary skill in the art. For example, 2-(bis-methylsulfanyl-methyleneamino)-1-(10,10-dimethyl-3,3-dioxo-3-thia-4-aza-tricyclo[5.2.1.0 1,5]dec-4-yl)-ethanone is described in *Tetrahedron Letters*, p. 6009, 1989.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 18

Preparation of 2-[4-(2-benzoylsulfanyl-3-phenyl-propionyl-amino)-3-oxo-1,3,4,5-tetrahydro-benzo[c] azepin-2-yl]-4-methyl-valeric acid, tert-butyl ester Step a: Methanesulfonic acid 2-(2-chloromethyl-phenyl)-ethyl ester Dissolve homophthalic acid (22.2 g, 0.123 mmol) in tetrahydrofuran (250 mL) and add dropwise at room temperature to a slurry of lithium aluminum hydride (15.5 g, 0.407 mol) in tetrahydrofuran (500 mL). Heat at reflux for 18 hours, cool in an ice bath and carefully add, by dropwise addition, water (16 mL), followed by 50% sodium hydroxide (16 mL). Remove the ice bath, add water slowly with stirring and stir until the gray precipitate turns white and evolution of gas ceases. Filter, wash solids with methylene chloride, dry ($MgSO_4$) and evaporate the solvent in vacuo to give 2-(2-hydroxymethyl-phenyl)-ethanol as a viscous oil (18.4 g, 98%).

Mix 2-(2-hydroxymethyl-phenyl)-ethanol (12.0 g, 78.8 mmol) and collidine (23 mL, 0.17 mol) and treat with lithium chloride (7.35 g, 0.173 mmol) in dimethylformamide (125 mL). Cool in an ice bath and treat, by dropwise addition, with mesyl chloride (13.4 mL). Stir at 0° C. for 4 hours, partition between ice water (300 mL) and a 1:1 mixture of ether:pentane (2×400 mL). Wash the organic layer with a saturated solution of $CuSO_4$ (2×200 mL), dry ($MgSO_4$) and purify by silica gel chromatography (2.5:1 hexane/ethyl acetate followed by 2:1 hexane/ethyl acetate followed by 3:2 hexane/ethyl acetate) to give the title compound as a pale yellow oil (8.8 g, 45%).

Step b: 1-Iodomethyl-2-vinyl-benzene

Dissolve methanesulfonic acid 2-(2-chloromethyl-phenyl)-ethyl ester (8.8 g, 35.4 mmol) in ether (80 mL) and cool to −35° C. Add potassium t-butoxide (10 g, 89 mmol) and stir for 30 minutes. Add water (50 mL) and ether (150 mL), extract, dry ($Na_2SO_4$) and purify by silica gel chromatography (2:3 methylene chloride/pentane) to give 1-chloromethyl-2-vinyl-benzene as a colorless oil (4.43 g, 82%).

Dissolve 1-chloromethyl-2-vinyl-benzene (4.0 g, 26 mmol) in acetone (100 mL) and add sodium iodide (4.5 g, 30 mmol). Heat at gentle reflux for 30 minutes. Cool, add water (150 mL) and extract with pentane (200 mL). Dry ($MgSO_4$) and evaporate the solvent in vacuo to give the title compound (95%).

Step c: 2-(Bis-methylsulfanyl-methyleneamino)-1-(10,10-dimethyl-3,3-dioxo-3-thia-4-aza-tricyclo[5.2.1.0 1,5]dec-4-yl)-3-(2-vinyl-phenyl)-propan-1-one Dissolve 2-(bis-methylsulfanyl-methyleneamino)-1-(10, 10-dimethyl-3,3-dioxo-3-thia-4-aza-tricyclo[5.2.1.0 1,5] dec-4-yl)-ethanone (7.91 g, 21.0 mmol) in tetrahydrofuran (100 mL) and cool to −78° C. Treat, by dropwise addition, with 1.6M n-butyllithium in hexane (13.1 mL, 21 mmol). Stir for 1.5 hours, then add hexamethylphosphotriamide (HMPA) (4.25 mL, 24.4 mmol). Stir for 15 minutes and add, via cannula, a solution of 1-iodomethyl-2-vinyl-benzene (6.1 g, 25 mmol) in tetrahydrofuran (100 mL). Stir overnight at room temperature, partition between saturated ammonium chloride (2×75 mL) and ethyl acetate (400 mL). Dry ($Na_2SO_4$) and purify by silica gel chromatography (2.5:1 hexane/ethyl acetate) to give the title compound as a white solid (4.5 g).

Step d: 2-Amino-3-(2-vinyl-phenyl)-propionic acid

Dissolve 2-(bis-methylsulfanyl-methyleneamino)-1-(10, 10-dimethyl-3,3-dioxo-3-thia-4-aza-tricyclo[5.2.1.0 1,5] dec-4-yl)-3-(2-vinyl-phenyl)-propan-1-one (5.21 g, 10.6 mmol) in tetrahydrofuran (100 mL) and ) and 0.75N hydrochloric acid (100 mL). Stir at room temperature for 24 hours, evaporate the solvent in vacuo to give the hydrochloride salt as a white solid. Dissolve in tetrahydrofuran (200 mL) and water (50 m), add lithium hydroxide monohydrate (1.9 g, 4.5 mmol) and stir at room temperature under a nitrogen atmosphere for 4 hours. Extract into methylene chloride (200 mL) and wash with 2N sodium hydroxide (50 mL). Acidify to pH 2–3 while cooling in an ice bath and concentrate in vacuo to give the title compound as an off-white solid (3.40 g, 100%).

Step e: 2-(1,3-Dioxo-1,3-dihydro-isoindol-2-yl)-3-(2-vinyl-phenyl)-propionic acid Dissolve 2-amino-3-(2-vinyl-phenyl)-propionic acid (3.40 g) in water (75 mL) and add sodium carbonate (1.97 g, 18.6 mmol) and N-carbethoxyphthalimide (2.81 g, 12.8 mmol). Stir for 2.5 hours, wash with methylene chloride (200 mL), acidify to pH 1 with cold concentrated hydrochloric acid and extract with ethyl acetate (3×200 mL), dry ($Na_2SO_4$), evaporate the solvent in vacuo and purify by silica gel chromatography (1:1:2% hexane/ethyl acetate/ acetic acid) followed by recrystallization (isopropranol) to give the title compound as a pale yellow solid (2.47 g).

Step f: 2-(1,3-Dioxo-1,3-dihydro-isoindol-2-yl)-3-(2-vinyl-phenyl)-propionic acid, 2-trimethylsilanyl-ethyl ester Dissolve 2-(1,3-dioxo-1,3-dihydro-isoindol-2-yl)-3-(2-vinyl-phenyl)-propionic acid (2.47 g, 7.69 mmol) in tetrahydrofuran (35 mL) and cool in an ice bath. Treat with pyridine (1.6 mL, 20 mmol) and 2-(trimethylsilyl)ethanol (2.3 mL, 16 mmol). Stir for 30 minutes and add 1-(3-dimethylaminopropyl)-3-ethylcarbodiimide hydrochloride (EDC) (2.21 g, 11.5 mmol). Stir for 22 hours at 5° C., then at room temperature for 1.5 hours. Cool to 0° C., add 0.6 times all reagents and stir at room temperature overnight. Dilute with ethyl acetate (150 mL), wash with 5% sulfuric acid (40 mL) and saturated sodium hydrogen carbonate (40 mL). Back extract with methylene chloride (100 mL), wash with brine (30 mL) and dry ($Na_2SO_4$). Evaporate the solvent in vacuo and purify by silica gel chromatography (2:1 hexane/ethyl acetate) to give the title compound (2.61 g, 81%).

Step g: 2-(1,3-Dioxo-1,3-dihydro-isoindol-2-yl)-3-(2-formyl-phenyl)-propionic acid, 2-trimethylsilanyl-ethyl ester Dissolve 2-(1,3-dioxo-1,3-dihydro-isoindol-2-yl)-3-(2-vinyl-phenyl)-propionic acid, 2-trimethylsilanyl-ethyl ester (2.61 g, 6.19 mmol) in methylene chloride (70 mL) and methanol (75 mL). Cool to −78° C. and treat with ozone until a blue color persists. Purge with nitrogen and add dimethylsulfide (7 mL) and pyridine (0.35 mL). Allow to warm to room temperature gradually overnight. Partition between methylene chloride (100 mL) and water (40 mL). Extract the aqueous with methylene chloride (50 mL), dry ($Na_2SO_4$) and purify by silica gel chromatography (2.5:1 hexane/ethyl acetate) to give the title compound as a colorless viscous oil (2.65 g, 100%).

Step h: 2-{2-[2-(1,3-Dioxo-1,3-dihydro-isoindol-2-yl)-2-(2-trimethylsilanyl-ethoxycarbonyl)-ethyl]-benzylamino}-4-methyl-valeric acid, tert-butyl ester Dissolve 2-(1,3-dioxo-1,3-dihydro-isoindol-2-yl)-3-(2-formyl-phenyl)-propionic acid, 2-trimethylsilanyl-ethyl ester (250 mg, 0.590 mmol) in methanol (15 mL) and treat with L-leucine tert-butyl ester hydrochloride (0.66 g, 3.0 mmol). Stir at room temperature for 2 hours with 3A molecular sieves, add sodium cyanoborohydride (0.6 mL of a 1.0M solution in tetrahydrofuran, 0.6 mmol), stir for 0.5 hours, add additional sodium cyanoborohydride (0.3 mL) and stir for 5 hours. Filter through filter aid, evaporate the solvent in vacuo and partition the residue between methylene chloride (100 mL) and saturated sodium hydrogen carbonate (40 mL). Dry ($Na_2SO_4$), evaporate the solvent in vacuo and purify by silica gel chromatography (5:1 hexane/ethyl acetate followed by 3:1 hexane/ethyl acetate) to give the title compound (221 mg, 63%).

Step i: 2-{2-[2-Carboxy-2-(1,3-dioxo-1,3-dihydro-isoindol-2-yl)-ethyl]-benzylamino}-4-methyl-valeric acid, tert-butyl ester Dissolve 2-{2-[2-(1,3-dioxo-1,3-dihydro-isoindol-2-yl)-2-(2-trimethylsilanyl-ethoxycarbonyl)-ethyl]-benzylamino}-4-methyl-valeric acid, tert-butyl ester (221 mg, 0.372 mmol) in tetrahydrofuran (5 mL) and treat with tetrabutylammonium fluoride (0.43 mL of a 1.0M solution in tetrahydrofuran, 0.43 mmol). Stir for 1.5 hours, evaporate the solvent in vacuo and dissolve the residue in ethyl acetate (75 mL). Wash with 1N hydrochloric acid (25 mL) and brine (25 mL). Dry ($Na_2SO_4$) and evaporate the solvent in vacuo to give the title compound as a white solid (188 mg).

Step j: 2-[4-((1,3-Dioxo-1,3-dihydro-isoindol-2-yl)-3-oxo-1,3,4,5-tetrahydro-benzo[c]azepin-2-yl]-4-methyl-valeric acid, tert-butyl ester Dissolve 2-{2-[2-carboxy-2-(1,3-dioxo-1,3-dihydro-isoindol-2-yl)-ethyl]-benzylamino}-4-methyl-valeric acid, tert-butyl ester (188 mg) in tetrahydrofuran (10 mL) and cool in an ice bath. Add sequentially, N-methylmorpholine (86 μL, 0.78 mmol), and isobutylchloroformate (55 μL, 0.43 mmol). Stir for 2 hours, filter, wash salts with dry tetrahydrofuran, evaporate the solvent in vacuo and purify by silica gel chromatography (1:1 hexane/ethyl acetate) to give the title compound as a white solid (64 mg, 93%).

Step k: 2-(4-Amino-3-oxo-1,3,4,5-tetrahydro-benzo[c]azepin-2-yl)-4-methyl-valeric acid, tert-butyl ester Dissolve 2-[4-((1,3-dioxo-1,3-dihydro-isoindol-2-yl)-3-oxo-1,3,4,5-tetrahydro-benzo[c]azepin-2-yl]-4-methyl-valeric acid, tert-butyl ester (160 mg, 0.336 mmol) in methanol (3 mL) and treat with a solution of hydrazine monohydrate (0.40 mL, 0.40 mmol) in methanol. Stir at room temperature for 65 hours, filter through filter aid, wash with methylene chloride, filter through filter aid and dry ($MgSO_4$). Evaporate the solvent in vacuo to give the title compound (93 mg, 80.2%).

Step l: 2-[4-(2-Benzoylsulfanyl-3-phenyl-propionyl-amino)-3-oxo-1,3,4,5-tetrahydro-benzo[c]azepin-2-yl]-4-methyl-valeric acid, tert-butyl ester Dissolve 2-(4-amino-3-oxo-1,3,4,5-tetrahydro-benzo[c]azepin-2-yl)-4-methyl-valeric acid, tert-butyl ester (93 mg, 0.27 mmol) in methylene chloride (3 mL) and treat with (S)-3-phenyl-2-benzoylthiopropionic acid (115 mg, 0.40 mmol) and EEDQ (100 mg, 0.40 mmol). Stir at room temperature for 18 hours, evaporate the solvent in vacuo, dissolve the residue in ethyl acetate (40 mL) and wash with 5% sulfuric acid (15 mL) when with saturated sodium hydrogen carbonate (15 mL). Dry ($Na_2SO_4$), evaporate the solvent in vacuo and purify by silica gel chromatography (6:1 hexane/ethyl acetate followed by 2.5:1 hexane/ethyl acetate) to give the title compound as a colorless oil (141 mg, 85%).

EXAMPLE 19

Preparation of 2-[4-(2-Benzoylsulfanyl-3-phenyl-propionyl-amino)-3-oxo-1,3,4,5-tetrahydro-benzo[c]azepin-2-yl]-4-methyl-valeric acid Dissolve 2-[4-(2-benzoylsulfanyl-3-phenyl-propionyl-amino)-3-oxo-1,3,4,5-tetrahydro-benzo[c]azepin-2-yl]-4-methyl-valeric acid, tert-butyl ester (141 mg, 0.229 mmol) in methylene chloride (5 mL) and treat with anisole (0.12 mL, 1.15 mmol) then with trifluoroacetic acid (1.5M). Stir at room temperature for 15 hours, partition between ethyl acetate (25 mL) and brine (15 mL). Wash the organic layer with brine (15 mL), dry ($Na_2SO_4$) and purify by silica gel chromatography (1:1 hexane/ethyl acetate followed by 1:1:0.01 hexane/ethyl acetate/acetic acid) to give the title compound as a white solid (157 mg).

EXAMPLE 20

Preparation of 2-[4-(2-Mercapto-3-phenyl-propionyl-amino)-3-oxo-1,3,4,5-tetrahydro-benzo[c]azepin-2-yl]-4-methyl-valeric acid Dissolve 2-[4-(2-benzoylsulfanyl-3-phenyl-propionyl-amino)-3-oxo-1,3,4,5-tetrahydro-benzo[c]azepin-2-yl]-4-methyl-valeric acid (0.229 mmol) in degassed methanol (3 mL) and cool in an ice bath. Treat with degassed 1N aqueous lithium hydroxide (1.0 mL) and stir, allowing the ice bath to warm gradually over 3 hours. With the reaction at 0° C., acidify with 5% hydrochloric acid. Partition between methylene chloride (75 mL) and water (25 mL), dry ($Na_2SO_4$) and purify by silica gel chromatography (3:1:0.01 hexane/ethyl acetate/acetic acid followed by 1:1:0.01 hexane/ethyl acetate/acetic acid to give the title compound as a white solid (84 mg, 80.8%).

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also modulate intestinal smooth muscle contractility and would be useful in the treatment of irritable bowel syndrome.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) will generally vary from about 0.01 milligram per kilogram of body weight per day (mg/kg/day) to about 20 mg/kg/day. A daily dose of from about 0.1 mg/kg to about 10 mg/kg is preferred.

In addition, the present invention further provides a method of inhibiting ACE in a patient in need thereof comprising administering to said patient an effective ACE inhibitory amount of a compound of Formula (I). A patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyper-aldosteronemic effects caused thereby. An effective ACE inhibitory amount of a compound of Formula (I) is that amount which is effective in inhibiting ACE in a patient in need thereof which results, for example, in a hypotensive effect. An effective ACE inhibitory amount and an effective ACE inhibitory dose are the same as that described above for an effective enkephalinase inhibitory amount and dose.

In addition, the present invention further provides a method for treating a patient suffering from smooth cell proliferation. An effective smooth cell proliferation inhibitory amount of a compound of Formula (I) is that amount which is effective in inhibiting smooth cell proliferation in a patient in need thereof which results, for example, in a reduced myointimal thickening after vascular injury. An effective smooth cell proliferation inhibitory amount and an effective smooth cell proliferation inhibitory dose are the same as that described above for an effective enkephalinase inhibitory amount and dose.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0.001% to about 75% of the composition by weight. Inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application.

The compounds of Formula (I) wherein $R_1$ is hydrogen or alkoxy are preferred. The compounds of Formula (I) wherein $R_2$ is hydrogen or alkoxy are preferred. In addition, compounds of Formula (I) wherein $R_3$ is are preferred.

The following specific compounds of Formula (I) are particularly preferred in the end-use application of the compounds of the present invention:

2-[4-(2-Thio-3-phenyl-propionyl-amino)-3-oxo-1,3,4,5-tetrahydro-benzo[c]azepin-2-yl]-4-methyl-valeric acid, (S)-N-1-(2-methylpropyl)-2-(thio)-ethylamine, disulfide;

2-[4-(2-Thio-3-phenyl-propionyl-amino)-3-oxo-1,3,4,5-tetrahydro-benzo[c]azepin-2-yl]-4-methyl-valeric acid, (R)-1-(2-methylpropyl)-2-(thio)-ethylamine, disulfide;

2-[4-(2-Thio-3-phenyl-propionyl-amino)-3-oxo-1,3,4,5-tetrahydro-benzo[c]azepin-2-yl]-4-methyl-valeric acid, L-cysteine ethyl ester, disulfide;

2-[4-(2-Thio-3-phenyl-propionyl-amino)-3-oxo-1,3,4,5-tetrahydro-benzo[c]azepin-2-yl]-4-methyl-valeric acid, benzylthio, disulfide;

2-[4-(2-Thio-3-phenyl-propionyl-amino)-3-oxo-1,3,4,5-tetrahydro-benzo[c]azepin-2-yl]-4-methyl-valeric acid, ethylthio, disulfide;

2-[4-(2-Thio-3-phenyl-propionyl-amino)-3-oxo-1,3,4,5-tetrahydro-benzo[c]azepin-2-yl]-4-methyl-valeric acid, disulfide, 2-hydroxyethylthio, disulfide;

2-[4-(2-Thio-3-phenyl-propionyl-amino)-3-oxo-1,3,4,5-tetrahydro-benzo[c]azepin-2-yl]-4-methyl-valeric acid, 2-pyridylmethylthio, disulfide;

2-[4-(2-Thio-3-phenyl-propionyl-amino)-3-oxo-1,3,4,5-tetrahydro-benzo[c]azepin-2-yl]-4-methyl-valeric acid, 2-thioacetic acid morpholine carboxamide, disulfide.

The following in vivo and ex vivo studies illustrate the utility of the compounds of the present invention as enkephalinase inhibitors and as ACE inhibitors. These studies are carried out by the method of J. F. French et al *J. Pharmcacol. Exp. Ther.*, 268(1), 180–186 (1994).

Administer test compound or vehicle (99/1, ethanol/1% sodium bicarbonate solution) to fasted male Sprague-Dawley rats (Charles Rivers Breeding Laboratories Inc.). Administration is carried out by intraperitoneal injection. At 3 hours after administration, sacrifice the rats and remove the kidneys and freeze. Homogenize whole kidneys and carry through the P2 step of the protocol of Booth and Kenny [*Biochem. J.*, 142, 575–581 (1974)] for the preparation of the microvilli fraction. Resuspend P2 material in 50 mM HEPES buffer, pH 8.0, containing 0.3M NaCl and 0.5% Triton X-100 and keep at −20° C. prior to the assay. The enzyme activity may be measured by the fluorometric methods of Florentin et al *Anal. Biochem.* 141, 62–69 (1984). The enzyme is assayed in 50 mM HEPES buffer (pH 7.4) in a 3.0 mL reaction volume containing 12 µM of the substrate dansyl-p-AlaGly (p-nitro)PheGly-OH (Km=40 µM) at 25° C. The enzyme in a small volume is added to initiate the reaction and the rate of fluorescence increase is recorded continuously using a fluorometer (excitation at 339 nm, emission at 562 nm). Use Thiorphan (Sigma Chemical Co.) as a standard for NEP inhibition in vitro. The effectiveness of the test compound is determined by measuring enzyme activity from kidneys obtained from test compound treated rats compared to enzyme activity from kidneys obtained from vehicle treated rats. The Thiorphan treated animal serve as a positive control. Determine ACE activity by the radiometric assay method of Ryan [J. W. Ryan, *Methods in Enzymatic Analysis*, 3rd ed., vol. 5, p. 20–34; ed. by J. Bergmeyer and M. Grassi, Verlag Chemie, Weinheim 1983] using tritiated hippuryl-glycyl-glycine (Ventrex Laboratories, Portland Me.). Buffer is used in the spectrophotometric ACE assay. After acid quench, tritiated product is extracted into Ventrex Cocktail 1 [B. N. Swanson et al, *Anal. Biochem.* 148, 401–407 (1985)] and count in a Beckman scintillation counter. Complete inhibition of radioactive product formation by 1 µM enalaprilat in the assay of either compound- or vehicle-dosed rat kidney preparations is taken to demonstrate specificity for ACE.

Anesthetize Sprague-Dawley male rats (Charles Rivers Breeding Laboratories Inc.) weighing 230–290 g with methoxyfluorane and pith by inserting a stainless steel rod (2.2 mm in diameter) through the right eye socket, through the brain and down the spinal column to the sacral region. Ventilate the rat's lungs through an endotracheal tube (Harvard Pump, Model 688). Ventilate at a rate of 12.5 mL/minute provided in 50 strokes. Record systemic blood pressure from a cannula (PE 50, containing 0.01% heparin) inserted into the left carotid artery and attached to a pressure transducer (P23 DC). Systemic blood pressure is recorded continuously during the test on a polygraph (Grass Model 70). Insert a 23 G hypodermic needle attached to a cannula (PE 50) into the lumen of the right femoral vein for injection of the test compound. Thirty minutes after pithing, give an intravenous injection of angiotensin I (0.3 μg). Angiotensin I (human) is made up in 0.01% ascorbic acid solution at a concentration of 0.3 μg/mL from a stock solution of 550 μg/mL in 0.01% acetic acid solution. Repeat the intravenous injection of angiotensin I (0.3 μg) at 10 minute intervals until two consecutive injections give responses that are within 10% of each other. Administer by intraperitoneal or by intravenous injection, either the test compound or vehicle. Administer an intravenous injection of angiotensin I (0.3 μg) at 15, 30, 45, 60, 90, and 120 minutes following administration of test compound or vehicle. The effectiveness of the test compound is determined by measuring the decrease in angiotensin I induced pressor response for test compound treated rats compared to vehicle treated rats.

What is claimed is:

1. A compound of the formula

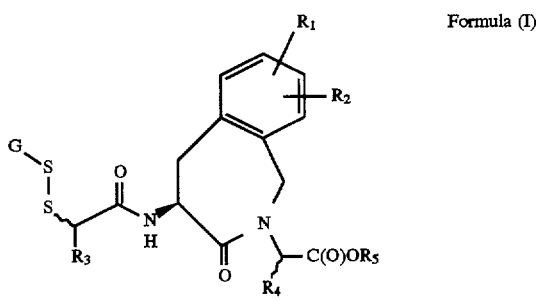

Formula (I)

wherein $R_1$ and $R_2$ are each independently hydrogen, hydroxy, —$OR_6$ wherein $R_6$ is a $C_1$–$C_4$ alkyl or an Ar—Y— group wherein Ar is aryl and Y is a $C_0$–$C_4$ alkyl; or, where $R_1$ and $R_2$ are attached to adjacent carbon atoms, $R_1$ and $R_2$ can be taken together with said adjacent carbons to form a benzene ring, or methylenedioxy;

$R_3$ is hydrogen, $C_1$–$C_8$ alkyl, —$CH_2OCH_2CH_2OCH_3$, or an Ar—Y— group;

$R_4$ is hydrogen, $C_1$–$C_6$ alkyl, an Ar—Y— group, —$CH_2CH_2SCH_3$, $CH_2OH$, $CH(OH)CH_3$, $CH_2CH_2C(=O)NH_2$, $CH_2C(=O)NH_2$, or a group of the formula

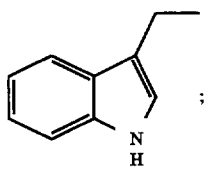

$R_5$ is hydrogen, a $C_1$–$C_4$ alkyl or an Ar—Y— group, or —$CH_2O$—$C(O)C(CH_3)_3$;

G is a radical chosen from the group;

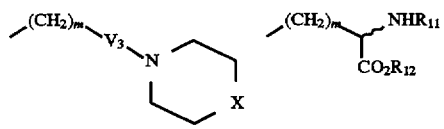

wherein m is an integer from 1 to 3;

$R_{11}$ is hydrogen, $C_1$–$C_6$ alkyl, or Ar—Y— group;

$R_{12}$ is hydrogen or $C_1$–$C_4$ alkyl;

$V_3$ is a direct bond or —C(O)—;

X is O;

or stereoisomers or pharmaceutically acceptable salts thereof.

2. A compound of claim 1 wherein $R_3$ is phenylmethyl.

3. A compound of claim 2 wherein $R_5$ is hydrogen.

4. A compound of claim 1 wherein the compound is 2-[4-(2-Thio-3-phenyl-propionyl-amino)-3-oxo-1,3,4,5-tetrahydro-benzo[c]azepin-2-yl]-4-methyl-valeric acid, L-cysteine ethyl ester, disulfide.

5. A compound of claim 1 wherein the compound is 2-[4-(2-Thio-3-phenyl-propionyl-amino)-3-oxo-1,3,4,5-tetrahydro-benzo[c]azepin-2-yl]-4-methyl-valeric acid, 2-thioacetic acid morpholine carboxamide, disulfide.

6. A method of inhibiting enkephalinase in a patient in need thereof comprising administering to said patient an effective enkephalinase inhibitory amount of a compound of formula

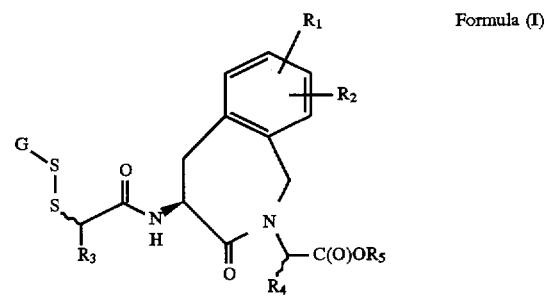

Formula (I)

wherein $R_1$ and $R_2$ are each independently hydrogen, hydroxy, —$OR_6$ wherein $R_6$ is a $C_1$–$C_4$ alkyl or an Ar—Y— group wherein Ar is aryl and Y is a $C_0$–$C_4$ alkyl; or, where $R_1$ and $R_2$ are attached to adjacent carbon atoms, $R_1$ and $R_2$ can be taken together with said adjacent carbons to form a benzene ring, or methylenedioxy;

$R_3$ is hydrogen, $C_1$–$C_8$ alkyl, —$CH_2OCH_2CH_2OCH_3$, or an Ar—Y— group;

$R_4$ is hydrogen, $C_1$–$C_6$ alkyl, an Ar—Y— group, —$CH_2CH_2SCH_3$, $CH_2OH$, $CH(OH)CH_3$, $CH_2CH_2C(=O)NH_2$, $CH_2C(=O)NH_2$, or a group of the formula

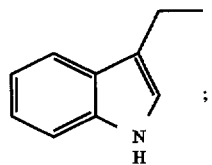

$R_5$ is hydrogen, a $C_1$–$C_4$ alkyl or an Ar—Y— group, or —$CH_2O$—$C(O)C(CH_3)_3$;

G is a radical chosen from the group;

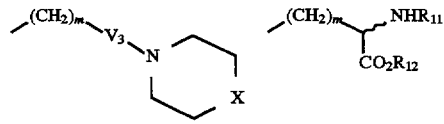

wherein m is an integer from 1 to 3;

$R_{11}$ is hydrogen, $C_1$–$C_6$ alkyl, or Ar—Y— group;

$R_{12}$ is hydrogen or $C_1$–$C_4$ alkyl;

$V_3$ is a direct bond or —C(O)—;

X is O;

or stereoisomers or pharmaceutically acceptable salts thereof.

7. A method according to claim 6 wherein the patient is in need of an endorphin- or enkephalin-mediated analgesic effect.

8. A method according to claim 6 wherein the patient is in need of an ANP-mediated hypotensive effect.

9. A method according to claim 6 wherein the patient is in need of an ANP-mediated diuretic effect.

10. A method according to claim 6 wherein the patient is suffering from congestive heart failure.

11. A method according to claim 6 wherein the patient is suffering from irritable bowel syndrome.

12. A method of inhibiting ACE in a patient in need thereof comprising administering to said patient an effective ACE inhibitory amount of a compound of formula Formula (I)

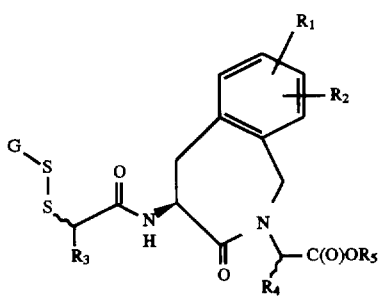

wherein $R_1$ and $R_2$ are each independently hydrogen, hydroxy, —$OR_6$ wherein $R_6$ is a $C_1$–$C_4$ alkyl or an Ar—Y— group wherein Ar is aryl and Y is a $C_0$–$C_4$ alkyl; or, where $R_1$ and $R_2$ are attached to adjacent carbon atoms, $R_1$ and $R_2$ can be taken together with said adjacent carbons to form a benzene ring, or methylenedioxy;

$R_3$ is hydrogen, $C_1$–$C_8$ alkyl, —$CH_2OCH_2CH_2OCH_3$, or an Ar—Y— group;

$R_4$ is hydrogen, $C_1$–$C_6$ alkyl, an Ar—Y— group, —$CH_2CH_2SCH_3$, $CH_2OH$, $CH(OH)CH_3$, $CH_2CH_2C(=O)NH_2$, $CH_2C(=O)NH_2$, or a group of the formula

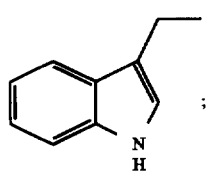

$R_5$ is hydrogen, a $C_1$–$C_4$ alkyl or an Ar—Y— group, or —$CH_2$—$O$—$C(O)C(CH_3)_3$;

G is a radical chosen from the group;

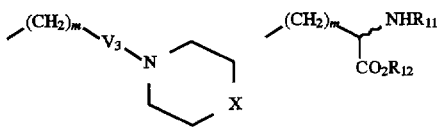

wherein m is an integer from 1 to 3;

$R_{11}$ is hydrogen, $C_1$–$C_6$ alkyl, or Ar—Y— group;

$R_{12}$ is hydrogen or $C_1$–$C_4$ alkyl;

$V_3$ is a direct bond or —C(O)—;

X is O;

or stereoisomers or pharmaceutically acceptable salts thereof.

13. A method according to claim 12 wherein the patient is in need of a hypotensive effect.

14. A method according to claim 12 wherein the patient is in need of a cognition enhancing effect.

15. A method according to claim 12 wherein the patient is suffering from congestive heart failure.

16. A method of inhibiting smooth cell proliferation in a patient in need thereof comprising administering to said patient an effective smooth cell proliferation inhibitory amount of a compound of formula Formula (I)

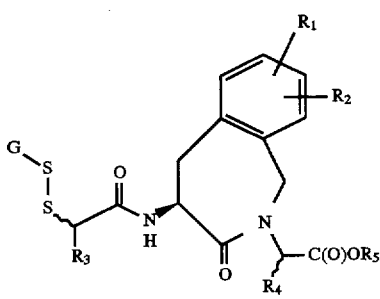

wherein $R_1$ and $R_2$ are each independently hydrogen, hydroxy, —$OR_6$ wherein $R_6$ is a $C_1$–$C_4$ alkyl or an Ar—Y— group wherein Ar is aryl and Y is a $C_0$–$C_4$ alkyl; or, where $R_1$ and $R_2$ are attached to adjacent carbon atoms, $R_1$ and $R_2$ can be taken together with said adjacent carbons to form a benzene ring, or methylenedioxy;

$R_3$ is hydrogen, $C_1$–$C_8$ alkyl, —$CH_2OCH_2CH_2OCH_3$, or an Ar—Y— group;

$R_4$ is hydrogen, $C_1$–$C_6$ alkyl, an Ar—Y— group, —$CH_2CH_2SCH_3$, $CH_2OH$, $CH(OH)CH_3$, $CH_2CH_2C(=O)NH_2$, $CH_2C(=O)NH_2$, or a group of the formula

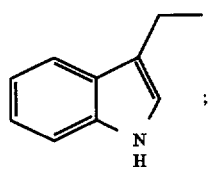

$R_5$ is hydrogen, a $C_1$–$C_4$ alkyl or an Ar—Y— group, or —$CH_2$—$O$—$C(O)C(CH_3)_3$;

G is a radical chosen from the group;

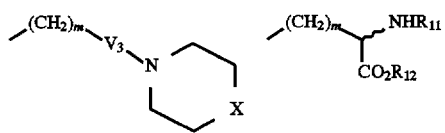

wherein
m is an integer from 1 to 3;
$R_{11}$ is hydrogen, $C_1$–$C_6$ alkyl, or Ar—Y— group;
$R_{12}$ is hydrogen or $C_1$–$C_4$ alkyl;
$V_3$ is a direct bond or —C(O)—;

X is O;

or stereoisomers or pharmaceutically acceptable salts thereof.

17. A composition comprising an assayable amount of a compound of claim 1 in admixture or otherwise in association with an inert carrier.

18. A pharmaceutical composition comprising an effective immunosuppressive amount of a compound of claim 1 in admixture or otherwise in association with one or more pharmaceutically acceptable carriers or excipients.

* * * * *